(12) United States Patent
Mizuno

(10) Patent No.: US 12,122,245 B2
(45) Date of Patent: Oct. 22, 2024

(54) ELECTRICALLY ASSISTED WHEELCHAIR, DRIVE UNIT, CONTROL METHOD AND COMPUTER PROGRAM

(71) Applicant: YAMAHA HATSUDOKI KABUSHIKI KAISHA, Iwata (JP)

(72) Inventor: Masamitsu Mizuno, Shizuoka (JP)

(73) Assignee: YAMAHA HATSUDOKI KABUSHIKI KAISHA, Shizuoka (JP)

( * ) Notice: Subject to any disclaimer, the term of this patent is extended or adjusted under 35 U.S.C. 154(b) by 283 days.

(21) Appl. No.: 17/688,183

(22) Filed: Mar. 7, 2022

(65) Prior Publication Data
US 2022/0289040 A1    Sep. 15, 2022

(30) Foreign Application Priority Data

Mar. 10, 2021   (JP) ................. 2021-038120

(51) Int. Cl.
*A61G 5/04* (2013.01)
*B60L 15/20* (2006.01)
*H02P 23/14* (2006.01)

(52) U.S. Cl.
CPC .............. *B60L 15/20* (2013.01); *A61G 5/048* (2016.11); *H02P 23/14* (2013.01); *A61G 2203/36* (2013.01); *A61G 2203/38* (2013.01); *B60L 2200/24* (2013.01)

(58) Field of Classification Search
CPC ..... B60L 15/20; B60L 2200/24; A61G 5/048; A61G 5/04; A61G 5/045; A61G 2203/36; A61G 2203/38; H02P 23/14
See application file for complete search history.

(56) References Cited

U.S. PATENT DOCUMENTS

| 5,818,189 A | 10/1998 | Uchiyama et al. |
| 10,285,881 B2 | 5/2019 | Kita |
| 2005/0279551 A1* | 12/2005 | LoPresti ............... G01S 17/931 180/167 |
| 2010/0036543 A1* | 2/2010 | Bitzer .................... A61G 5/048 701/1 |

(Continued)

FOREIGN PATENT DOCUMENTS

| EP | 3 061 435 A1 | 8/2016 |
| JP | H092371 A | 1/1997 |

(Continued)

OTHER PUBLICATIONS

KR 20170031822 A with machine translation (Year: 2017).*

(Continued)

*Primary Examiner* — Dino Kujundzic
(74) *Attorney, Agent, or Firm* — Keating & Bennett, LLP

(57) ABSTRACT

A drive unit usable in an electrically assisted wheelchair includes a controller to acquire an output signal from a torque sensor and an output signal from a speed sensor; measure a time period in which a first state, where the output signal from the torque sensor indicates that a forward-direction torque applied to a hand rim has a value no smaller than a first predetermined value, continues; and when the measured time period is a first time period or longer, start control of an electric motor in a cruise control mode by which the electrically assisted wheelchair runs while keeping a running speed at a target speed.

22 Claims, 13 Drawing Sheets

(56) References Cited

U.S. PATENT DOCUMENTS

| | | | |
|---|---|---|---|
| 2015/0298765 A1* | 10/2015 | Golden, Jr. | A61G 5/047 |
| | | | 180/206.3 |
| 2018/0224853 A1 | 8/2018 | Izhikevich | |
| 2020/0253798 A1 | 8/2020 | Mizuno et al. | |

FOREIGN PATENT DOCUMENTS

| | | | |
|---|---|---|---|
| JP | 2002-078752 A | | 3/2002 |
| JP | 3558314 B2 | * | 8/2004 |
| JP | 3703554 B2 | | 10/2005 |
| JP | 2020006038 A | | 1/2020 |
| JP | 2020509476 A | | 3/2020 |
| KR | 20140065291 A | * | 5/2014 |
| KR | 20170031822 A | * | 3/2017 |

OTHER PUBLICATIONS

KR 20140065291A Machine Translation (Year: 2014).*
JP 3558314 B2 with machine translation (Year: 2004).*
"Twion T24 | cruise mode function simply explained," Alber GmbH, Apr. 18, 2017, YouTube.com, https://youtu.be/QR7FyHqs_qk (video). (Year: 2017).*
"E-motion M25 | Power add-on drive for wheelchairs," Alber GmbH, Nov. 19, 2018, YouTube.com, https://youtu.be/1zj9ryFTXG0 (video). (Year: 2018).*
Official Communication issued in corresponding European Patent Application No. 22160476.2, mailed on Jul. 29, 2022.
Alber GmbH, "twion The electric drive for active wheelchairs", www.alber.de, 12 pages.
Alber, "E-Motion Mobility App, Operating instructions e-motion M25 Mobility App", 80 pages.

* cited by examiner

FIG.11
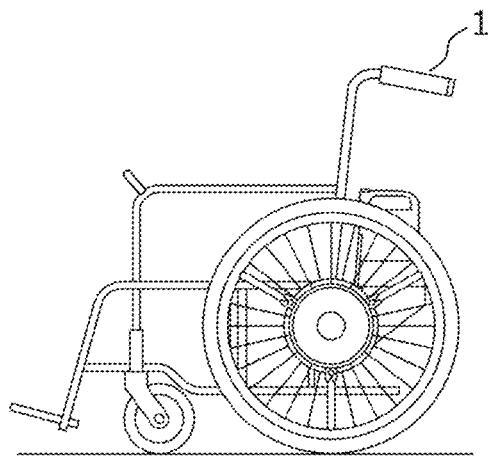
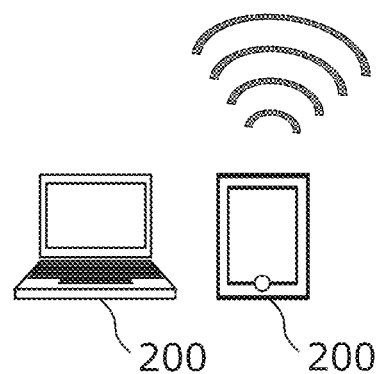

ELECTRICALLY ASSISTED WHEELCHAIR, DRIVE UNIT, CONTROL METHOD AND COMPUTER PROGRAM

CROSS REFERENCE TO RELATED APPLICATIONS

This application claims the benefit of priority to Japanese Patent Application No. 2021-038120 filed on Mar. 10, 2021. The entire contents of this application are hereby incorporated herein by reference.

BACKGROUND OF THE INVENTION

1. Field of the Invention

The present invention relates to an electrically assisted wheelchair, a drive unit, a control method and a computer program.

2. Description of the Related Art

An electrically assisted wheelchair uses an electric motor to assist a user who pushes hand rims with the power of his/her hands. The electrically assisted wheelchair causes the electric motor to generate driving power in accordance with human power applied to the hand rims by the user, and thus may alleviate the load imposed on the user pushing the hand rims.

Japanese Laid-Open Patent Publication No. 2002-078752 discloses an electrically assisted wheelchair having a cruise control function. When the cruise control is on, the running speed of the electrically assisted wheelchair is kept generally the same with no need for the user to push the hand rims. The running speed is kept generally the same regardless of the state of the road surface such as the gradient, steps or the like of the road surface, and therefore, the load on the user may be alleviated.

An operation panel included in the electrically assisted wheelchair disclosed in Japanese Laid-Open Patent Publication No. 2002-078752 includes a main power switch, a running switch with which a command to run is issued, and a speed setting volume switch with which the running speed is set. For turning on the cruise control, the user needs to take his/her hand off from the hand rim in order to use the hand to make an operation of turning on the main power switch, an operation of turning on the running switch and an operation of turning the running speed setting volume switch to set the running speed. The control of keeping the running speed the same is continued as long as the running switch is on.

For turning off the cruise control, the user needs to take his/her hand off from the hand rim in order to use the hand to turn off the running switch of the control panel. As can be seen, for turning on or off the cruise control, the user needs to make special operations other than the operation made on the hand rims, which causes a problem of increasing the load on the user.

The prior art technique needs further improvement in view of simplifying such an operation on the cruise control of an electrically assisted wheelchair.

SUMMARY OF THE INVENTION

A drive unit according to a preferred embodiment of the present invention is usable in an electrically assisted wheelchair and includes an electric motor to generate driving power to run the electrically assisted wheelchair; a torque sensor to output a signal in accordance with a torque transmitted from a hand rim to a wheel; a speed sensor to output a signal on a running speed of the electrically assisted wheelchair; and a controller configured or programmed to control a motion of the electric motor. The controller is configured or programmed to acquire the output signal from the torque sensor and the output signal from the speed sensor. The controller is configured or programmed to measure a time period in which a first state, where the output signal from the torque sensor indicates that a forward-direction torque applied to the hand rim has a value no smaller than a first predetermined value, continues. In a case where the measured time period is the first time period or longer, the controller is configured or programmed to start control of the electric motor in a cruise control mode by which the electrically assisted wheelchair runs while keeping the running speed at a target speed.

The electrically assisted wheelchair may start running in the cruise control mode by a simple operation, performed by the user, of applying power to the hand rim for a certain time period. The user does not need to perform any special operation to start running the electrically assisted wheelchair in the cruise control mode. Therefore, the convenience for the user may be improved.

In a preferred embodiment of the present invention, in a case where the running speed of the electrically assisted wheelchair is lower than a first speed, the controller does not need to start the control of the electric motor in the cruise control mode. In a case where the running speed is the first speed or higher and the measured time period is the first time period or longer, the controller may start the control of the electric motor in the cruise control mode.

If the cruise control mode is turned on while the electrically assisted wheelchair runs at a low speed in a small area, for example, indoors, the user may possibly feel uneasy. In the preferred embodiment in which the cruise control mode is set not to be turned on while the running speed is lower than the first speed, the convenience for the user may be improved.

In a preferred embodiment of the present invention, the controller may set, as the target speed, the running speed of the electrically assisted wheelchair at a time when a second time period elapses after the measured time period reaches the first time period.

In the preferred embodiment in which the running speed at a time when the second time period elapses is set as the target speed, the running speed obtained as a result of acceleration performed during the second time period may be set as the target speed. Therefore, the target speed may reflect the user's intention to increase the running speed by pushing the hand rim.

In a preferred embodiment of the present invention, in a case where the running speed keeps increasing after the second time period elapses, the controller may start the control of keeping the running speed at the target speed at a time when the running speed is decreased to the target speed.

In this preferred embodiment, after the second time period elapses, the electrically assisted wheelchair is further accelerated. Then, the electrically assisted wheelchair is mildly decelerated. During the mild deceleration, the control of keeping the running speed at the target speed is started. In this manner, the deviation of the actual change in speed from the change in speed imagined by the user operating the electrically assisted wheelchair may be reduced.

In a preferred embodiment of the present invention, the target speed may be preset.

In the preferred embodiment in which the target speed is preset, the electrically assisted wheelchair may run at the same speed each time. Even in a case where it is difficult to increase the running speed in accordance with the motion of the user pushing the hand rim, for example, even in a case where the electrically assisted wheelchair is on an upslope, the running speed is increased to the preset target speed by the cruise control. Therefore, the electrically assisted wheelchair may run at the speed intended by the user.

In a preferred embodiment of the present invention, in a case where the running speed keeps increasing after the first time period elapses and becomes higher than the target speed, the controller may start the control of keeping the running speed at the target speed at a time when the running speed is decreased to the target speed.

In this preferred embodiment, after the first time period elapses, the electrically assisted wheelchair is further accelerated. Then, the electrically assisted wheelchair is mildly decelerated. During the mild deceleration, the control of keeping the running speed at the target speed is started. In this manner, the deviation of the actual change in speed from the change in speed imagined by the user operating the electrically assisted wheelchair may be reduced.

In a preferred embodiment of the present invention, in a case where the running speed at a time when the first time period elapses is lower than the target speed, the controller may control the electric motor such that the running speed becomes the target speed, and then execute the control of keeping the running speed at the target speed.

This makes it unnecessary for the user to make an additional motion of increasing the running speed to the target speed, and thus may improve the convenience for the user.

In a preferred embodiment of the present invention, in a case where the output signal from the torque sensor indicates that the forward-direction torque applied to the hand rim has a value no smaller than the first predetermined value during the control of keeping the running speed at the target speed, the controller may control the electric motor such that a torque is generated having a value that is a sum of a torque to keep the running speed at the target speed and a torque in accordance with a level of the output signal.

Even during the execution of the cruise control, the running speed may be changed in accordance with the push operation made by the user to the hand rim. Therefore, the electrically assisted wheelchair may run as intended by the user.

The rotation rate of one of a pair of the wheels may be changed in accordance with the push operation made by the user to the corresponding hand rim among a pair of the hand rims. Therefore, the advancing direction of the electrically assisted wheelchair may be changed during the execution of the cruise control.

In a preferred embodiment of the present invention, in a case where the first state, where the output signal from the torque sensor indicates that the forward-direction torque applied to the hand rim has a value no smaller than the first predetermined value, continues for a third time period or longer during the control of keeping the running speed at the target speed, the controller may change the target speed to the running speed at a time when a fourth time period elapses after the first state continues for the third time period.

The electrically assisted wheelchair may run in a manner reflecting the user's intention to increase the running speed to be kept in the cruise control mode.

In a preferred embodiment of the present invention, in a case where a second state, where the output signal from the torque sensor indicates that a rearward-direction torque applied to the hand rim has a value no smaller than a second predetermined value, continues for a fifth time period, the controller may finish the control in the cruise control mode.

The user may finish the cruise control mode by a simple operation of applying power to the hand rim in the rearward direction for a certain time period. This may improve the convenience for the user.

In general, for significantly changing the advancing direction of, or stopping, the electrically assisted wheelchair, the user may make an operation of applying power to the hand rim in the rearward direction. In the same manner of operation as this, the user may finish the cruise control mode. Therefore, the user may operate the electrically assisted wheelchair by substantially the same sense as for a conventional wheelchair.

In accordance with an operation made by the user to one of the pair of hand rims in the rearward direction, the cruise control mode may be finished on the corresponding side. In this manner, the advancing direction of the electrically assisted wheelchair may be changed easily.

In a preferred embodiment of the present invention, in a case where the running speed of the electrically assisted wheelchair is decreased to a speed no higher than a second speed, which is lower than the target speed, during the control of keeping the running speed at the target speed, the controller may finish the control in the cruise control mode.

In a case where it becomes difficult to keep the target speed merely by the driving power generated by the electric motor, for example, in a case where the electrically assisted wheelchair is on an upslope having a large inclining angle, the cruise control mode may be finished and the electrically assisted wheelchair may be run by power that is a sum of the human power and the driving power provided by the electric motor. In this manner, the electrically assisted wheelchair may keep running.

In a preferred embodiment of the present invention, in a case where a state where a command value to drive the electric motor is a threshold value or larger continues for a sixth time period, the controller may finish the control in the cruise control mode.

In a case where a state where the electric motor is caused to generate a large driving power continues for a certain time period, the cruise control mode may be finished and the electrically assisted wheelchair may be run by power that is a sum of the human power and the driving power provided by the electric motor. This allows the electrically assisted wheelchair to keep running while the running speed is suppressed from being decreased.

In a preferred embodiment of the present invention, in a case where a battery that supplies electric power to drive the electric motor has a remaining capacity smaller than a threshold value, the controller may finish the control in the cruise control mode.

In a case where the remaining capacity of the battery is small, the control in the cruise control mode does not need to be executed. This may suppress the power consumption.

In a preferred embodiment of the present invention, the controller may acquire from an external device setting information on whether or not execution of the control in the cruise control mode is permissible. In a case where the setting information indicates that the execution of the control in the cruise control mode is permissible and the time period in which the first state continues is the first time period or longer, the controller may start the control in the cruise control mode. In a case where the setting information prohibits the execution of the control in the cruise control mode, the controller may not execute the control in the cruise control mode.

The external device may set whether or not the execution of the control in the cruise control mode is permissible. For example, while the electrically assisted wheelchair is in an area that is not suitable to running in the cruise control mode, the external device transmits to the drive unit setting information that prohibits the execution of the control in the cruise control mode. In this manner, the electrically assisted wheelchair may run appropriately in the area.

In a preferred embodiment of the present invention, the controller may acquire from an external device target speed information indicating the target speed, and may set a value indicated by the target speed information as the target speed.

In the preferred embodiment in which the external device sets the target speed, the user sitting on the electrically assisted wheelchair does not need to set the target speed. This may improve the convenience for the user.

The external device may transmit to the drive unit target speed information indicating a target speed varying in accordance with the area in which the electrically assisted wheelchair runs. In this case, the electrically assisted wheelchair may run at the running speed suitable to the area where the electrically assisted wheelchair is running.

In a preferred embodiment of the present invention, the drive unit may further include a notifier to notify a user of the start and the finish of the control in the cruise control mode.

This allows the user to recognize the start and the finish of the control in the cruise control mode.

In a preferred embodiment of the present invention, the target speed may be changeable, and the drive unit may further include a notifier that, in a case where the target speed has been changed, notifies a user of information indicating that the target speed has been changed.

This allows the user to recognize that the target speed has been changed.

An electrically assisted wheelchair according to a preferred embodiment of the present invention includes the above-described drive unit, a wheel to which the driving power generated by the electric motor is transmitted, and a hand rim provided on the wheel.

The electrically assisted wheelchair may start running in the cruise control mode by a simple operation, made by the user, of applying power to the hand rim for a certain time period. The user does not need to make any special operation to start running the electrically assisted wheelchair in the cruise control mode. Therefore, the convenience for the user may be improved.

A method according to a preferred embodiment of the present invention controls an electrically assisted wheelchair. The electrically assisted wheelchair includes an electric motor to generate driving power to run the electrically assisted wheelchair, a wheel to which the driving power generated by the electric motor is transmitted, a hand rim provided on the wheel, a torque sensor to output a signal in accordance with a torque transmitted from the hand rim to the wheel, and a speed sensor to output a signal on a running speed of the electrically assisted wheelchair. The method includes acquiring the output signal from the torque sensor and the output signal from the speed sensor; measuring a time period in which a first state, where the output signal from the torque sensor indicates that a forward-direction torque applied to the hand rim has a value no smaller than a first predetermined value, continues; and in a case where the measured time period is the first time period or longer, starting control of the electric motor in a cruise control mode by which the electrically assisted wheelchair runs while keeping the running speed at a target speed.

The electrically assisted wheelchair may start running in the cruise control mode by a simple operation, made by the user, of applying power to the hand rim for a certain time period. The user does not need to make any special operation to start running the electrically assisted wheelchair in the cruise control mode. Therefore, the convenience for the user may be improved.

A computer-readable non-transitory storage medium according to a preferred embodiment of the present invention includes a computer program to cause a computer to control an electrically assisted wheelchair. The electrically assisted wheelchair includes an electric motor to generate driving power to run the electrically assisted wheelchair, a wheel to which the driving power generated by the electric motor is transmitted, a hand rim provided on the wheel, a torque sensor to output a signal in accordance with a torque transmitted from the hand rim to the wheel, and a speed sensor to output a signal on a running speed of the electrically assisted wheelchair. The computer program causes the computer to execute acquiring the output signal from the torque sensor and the output signal from the speed sensor; measuring a time period in which a first state, where the output signal from the torque sensor indicates that a forward-direction torque applied to the hand rim has a value no smaller than a first predetermined value, continues; and in a case where the measured time period is the first time period or longer, starting control of the electric motor in a cruise control mode by which the electrically assisted wheelchair runs while keeping the running speed at a target speed.

The electrically assisted wheelchair may start running in the cruise control mode by a simple operation, made by the user, of applying power to the hand rim for a certain time period. The user does not need to make any special operation to start running the electrically assisted wheelchair in the cruise control mode. Therefore, the convenience for the user may be improved.

In a preferred embodiment of the present invention, the electrically assisted wheelchair may start running in the cruise control mode by a simple operation, made by the user, of applying power to the hand rim for a certain time period. The user does not need to make any special operation to start running the electrically assisted wheelchair in the cruise control mode. Therefore, the convenience for the user may be improved.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 11 shows the electrically assisted wheelchair 1 and an external device 200 according to a preferred embodiment of the present invention.

DETAILED DESCRIPTION OF THE PREFERRED EMBODIMENTS

Hereinafter, an electrically assisted wheelchair, a drive unit, a control method and a computer program according to preferred embodiments of the present invention will be described with reference to the drawings. In the description of the preferred embodiments, like components will bear like reference signs, and overlapping descriptions will be omitted. In the preferred embodiments, "front", "rear", "left", "right", "up" and "down" refer to front, rear, left, right, up and down as seen from a user sitting on a seat of an electrically assisted wheelchair. The following preferred embodiments are mere examples, and do not limit the present invention in any way.

Figure 1:
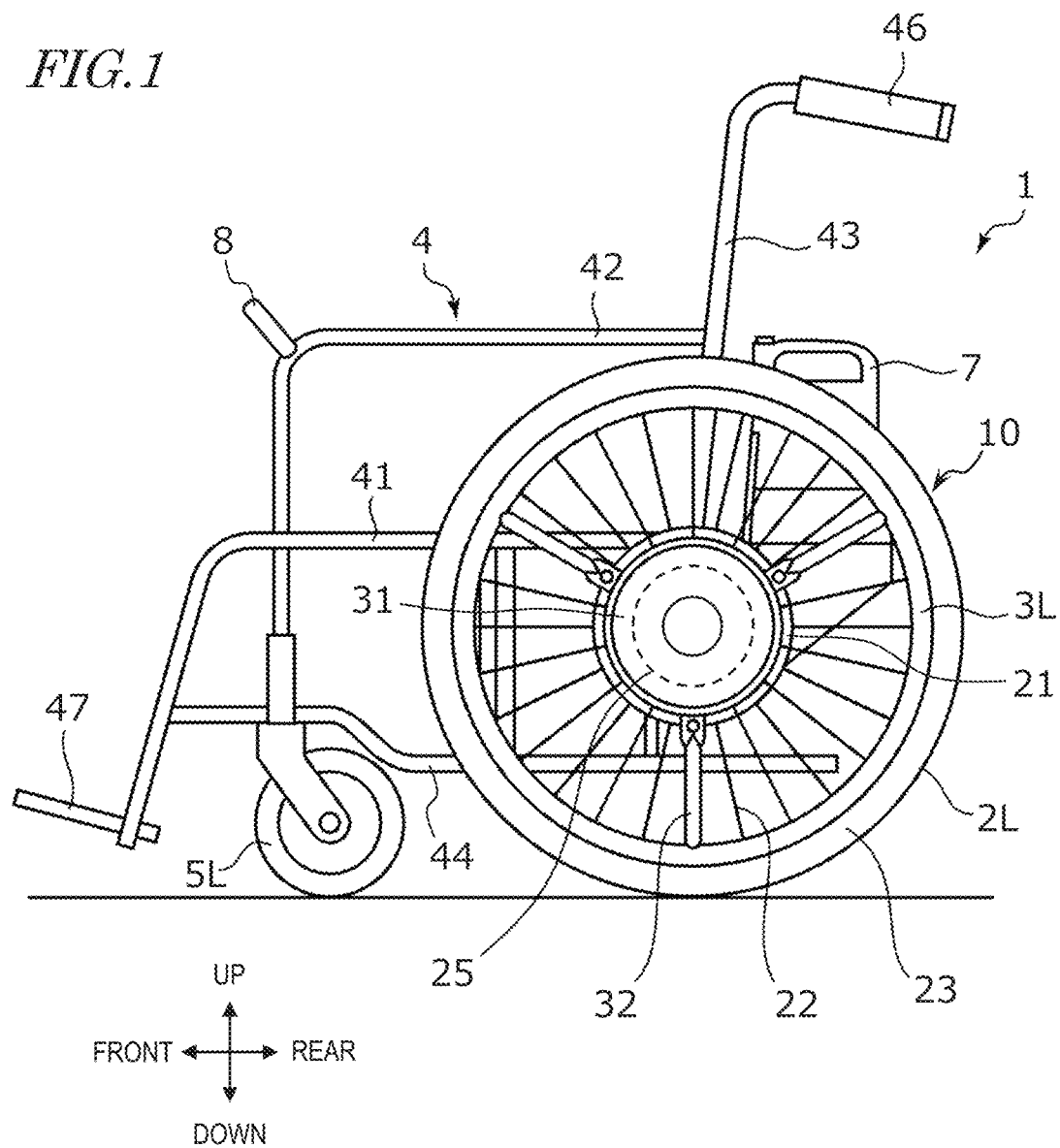
FIG. 1 is a left side view of an electrically assisted wheelchair 1 according to a preferred embodiment of the present invention.
Figure 2:
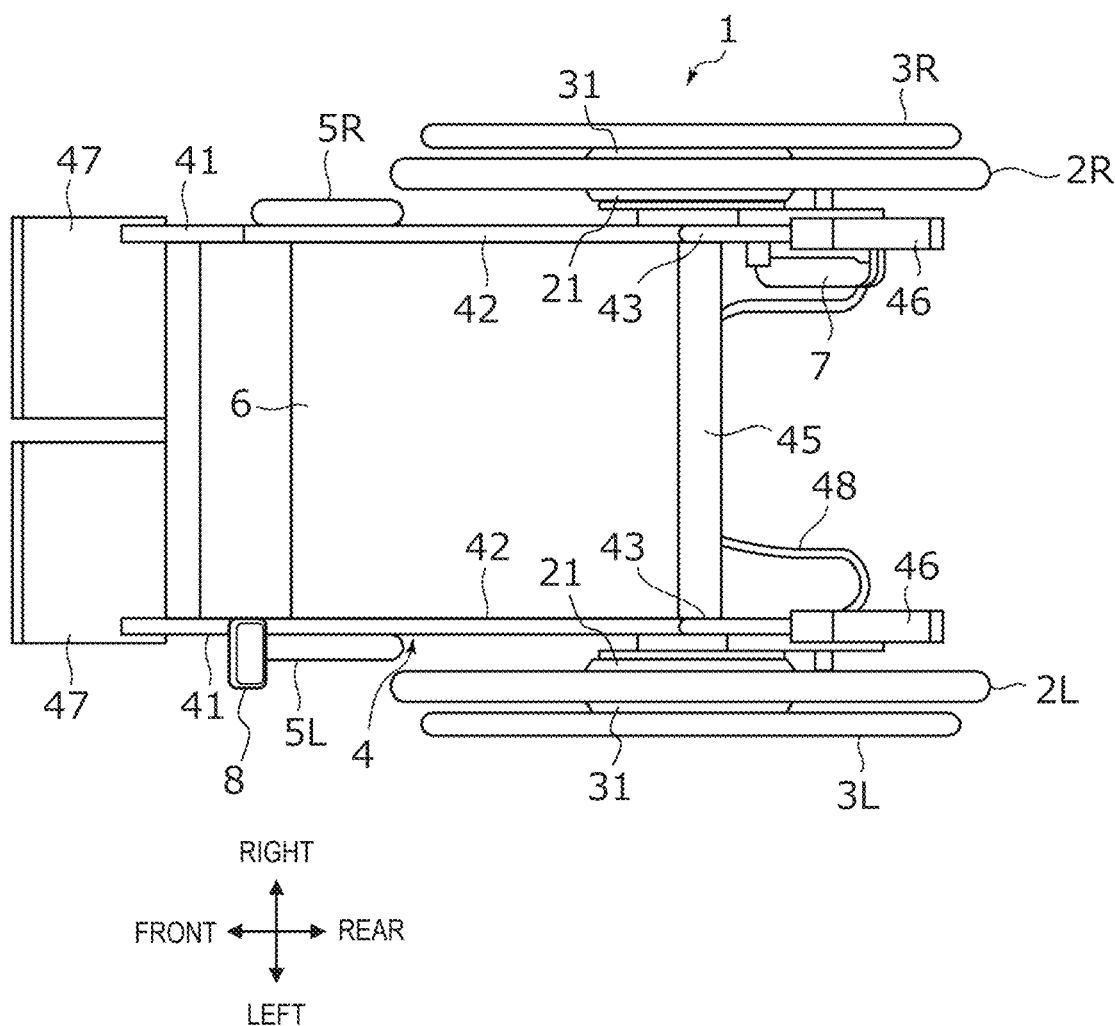
FIG. 2 is a plan view of the electrically assisted wheelchair 1 according to a preferred embodiment of the present invention.

FIG. 1 is a left side view of an electrically assisted wheelchair 1 according to a preferred embodiment of the present invention. FIG. 2 is a plan view of the electrically assisted wheelchair 1.

The electrically assisted wheelchair 1 includes a vehicle frame 4 made of a metal pipe or the like. A pair of (i.e., left and right) wheels 2L and 2R and a pair of (i.e., left and right) casters 5L and 5R are rotatably supported by the vehicle frame 4. The vehicle frame 4 includes a pair of (i.e., left and right) seat frames 41, a pair of (i.e., left and right) arm rests 42, a pair of (i.e., left and right) back frames 43, and a pair of (i.e., left and right) under frames 44.

The seat frames 41 extend forward from positions in the vicinity of axles of the wheels 2L and 2R. A seat 6, on which the user is to sit, is provided between the pair of seat frames 41. Front portions of the seat frames 41 are bent downward, and foot rests 47 are provided at bottom ends of the front portions of the seat frames 41. Rear ends of the seat frames 41 are connected with the back frames 43. The back frames 43 extend in an up-down direction. Top portions of the back frames 43 are bent rearward, and are provided with hand grips 46 for a care provider of the user. A back support 45 is provided between the pair of back frames 43.

The under frames 44 extend in a front-rear direction below the seat frames 41. Front ends of the under frames 44 are connected with the front portions of the seat frames 41. Rear portions of the under frames 44 are connected with bottom ends of the back frames 43. The arm rests 42 are located above the seat frames 41. Rear ends of the arm rests 42 are connected with the back frames 43. Front portions of the arm rests 42 are bent downward and are connected with the seat frames 41 and the under frames 44. One of the arm rests 42 is provided with a notification device 8 to notify the user of the state of the electrically assisted wheelchair 1.

A hand rim 3L, with which the wheel 2L is driven by human power, is provided on the wheel 2L. A hand rim 3R, with which the wheel 2R is driven by human power, is provided on the wheel 2R. The wheels 2L and 2R each include a wheel hub 21, an outer circumferential portion 23 enclosing the wheel hub 21, and a plurality of spokes 22. The plurality of spokes 22 connect the wheel hub 21 and the outer circumferential portion 23 to each other. The outer circumferential portion 23 includes a rim connected with the spokes 22 and a tire attached to the rim.

A rim base 31 is provided outward of each of the wheel hubs 21 in a left-right direction of the electrically assisted wheelchair 1. The hand rim 3L is connected with a plurality of connection pipes 32 extending radially from the rim base 31 of the wheel 2L. Similarly, the hand rim 3R is connected with a plurality of connection pipes 32 extending radially from the rim base 31 of the wheel 2R.

The wheel hubs 21 are each provided with an electric motor 25. The electric motor 25 is, for example, a hub motor. The wheel hub 21 includes an axle, a first housing located at an inner position in the left-right direction of the electrically assisted wheelchair 1 and a second housing located at an outer position in the left-right direction. The first housing at the inner position is secured to the axle, and the second housing at the outer position is rotatable with respect to the axle. A stator of the electric motor 25 is secured to the first housing and the axle, and a rotor of the electric motor 25 is secured to the second housing. The plurality of spokes 22 are connected with the second housing.

The axle of the wheel hub 21 is secured to the vehicle frame 4. The axle of the wheel hub 21 is secured to, for example, the back frame 43. The axle of the wheel hub 21 may be connected with the vehicle frame 4 via a bracket provided between the seat frame 41 and the under frame 44. The second housing rotates with respect to the axle and the first housing secured to the vehicle frame 4, and thus each of the wheels 2L and 2R rotates.

The electrically assisted wheelchair 1 includes a battery 7 to supply electric power to the electric motors 25. When the electric power is supplied to the electric motors 25, the rotors secured to the second housings rotate with respect to the stators secured to the first housings, and thus the wheels 2L and 2R rotate.

The electric motors 25 are not limited to being hub motors, and may be provided outward of the wheel hubs 21. In this case, the rotations generated by the electric motors 25 may be transmitted to the wheel hubs 21 via decelerators.

Now, a drive unit included in the electrically assisted wheelchair 1 will be described.

Figure 3:
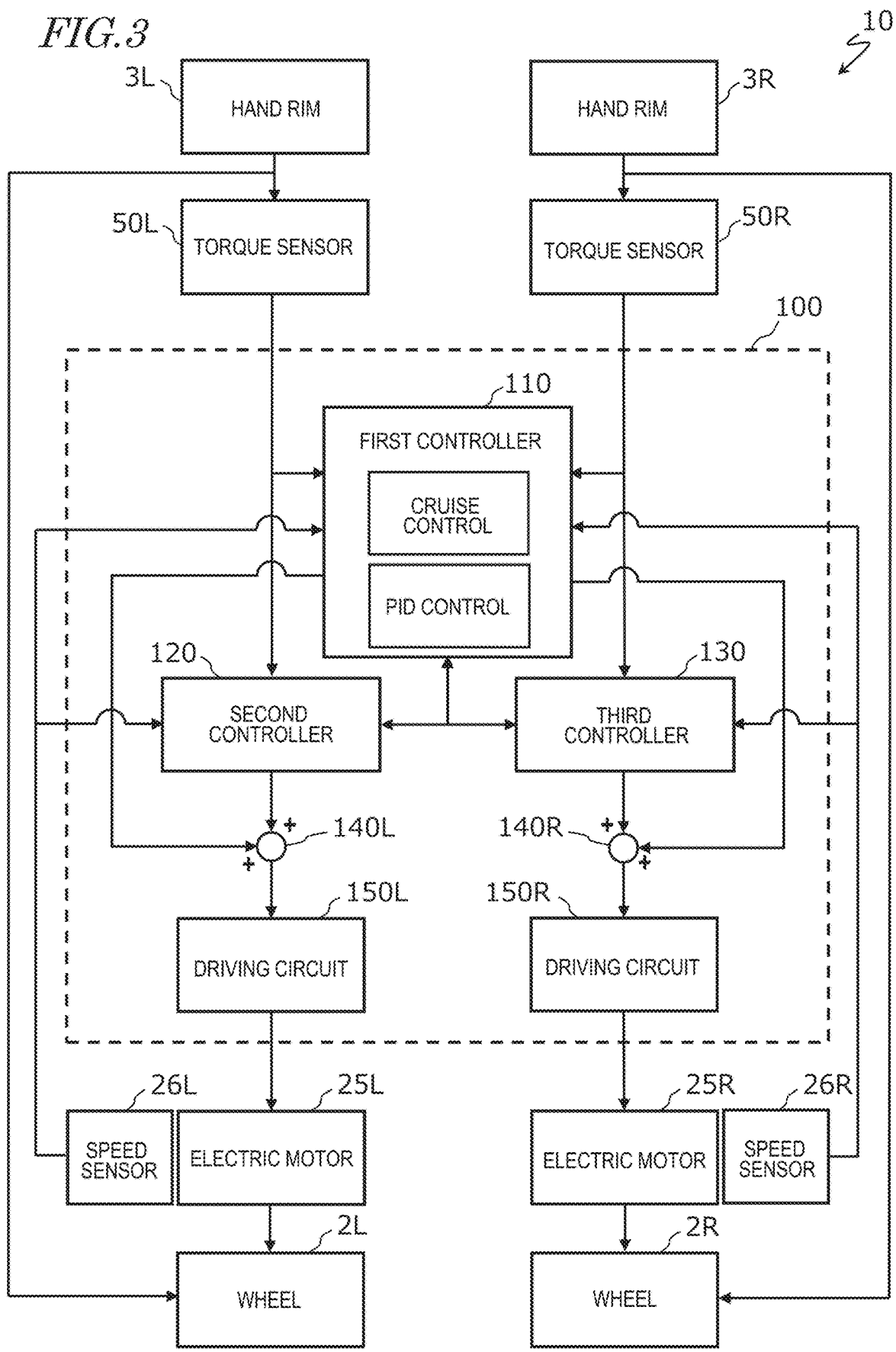
FIG. 3 is a block diagram showing a drive unit 10 according to a preferred embodiment of the present invention.

FIG. 3 is a block diagram showing a drive unit 10 included in the electrically assisted wheelchair 1. The drive unit 10 causes the electric motors 25 to generate driving power in accordance with the human power applied by the user to the hand rims 3L and 3R. The drive unit 10 also causes the driving motors 25 to generate driving power to execute a cruise control by which the electrically assisted wheelchair 1 runs while keeping the running speed at a target speed.

The drive unit 10 includes a controller 100, the electric motors 25L and 25R, speed sensors 26L and 26R, torque sensors 50L and 50R, the wheels 2L and 2R, and the hand rims 3L and 3R. The controller 100 includes a first controller 110, a second controller 120, a third controller 130, addition circuits 140L and 140R, and driving circuits 150L and 150R. The electric motor 25L is the electric motor 25 provided in the wheel 2L. The electric motor 25R is the electric motor 25 provided in the wheel 2R.

The second controller 120, the addition circuit 140L, the driving circuit 150L, the electric motor 25L, the speed sensor 26L and the torque sensor 50L may be provided in the wheel hub 21 of the wheel 2L. The third controller 130, the addition circuit 140R, the driving circuit 150R, the electric motor 25R, the speed sensor 26R and the torque sensor 50R may be provided in the wheel hub 21 of the wheel 2R. The first controller 110 may be provided in the wheel hub 21 of the wheel 2L or the wheel 2R.

The battery 7 (FIG. 2) supplies electric power to the drive unit 10. The electrically assisted wheelchair 1 includes a cable 48 (FIG. 2) extending in the left-right direction at a position to the rear of the back support 45. The cable 48 includes a power supply line and a communication line. In the example shown in FIG. 2, the battery 7 is detachably attached to a right rear portion of the vehicle frame 4. The components of the drive unit 10 provided on the wheel 2L side are supplied with electric power from the battery 7 via the cable 48. The first controller 110, the second controller 120 and the third controller 130 are communicable with each other via the cable 48.

Figure 4:
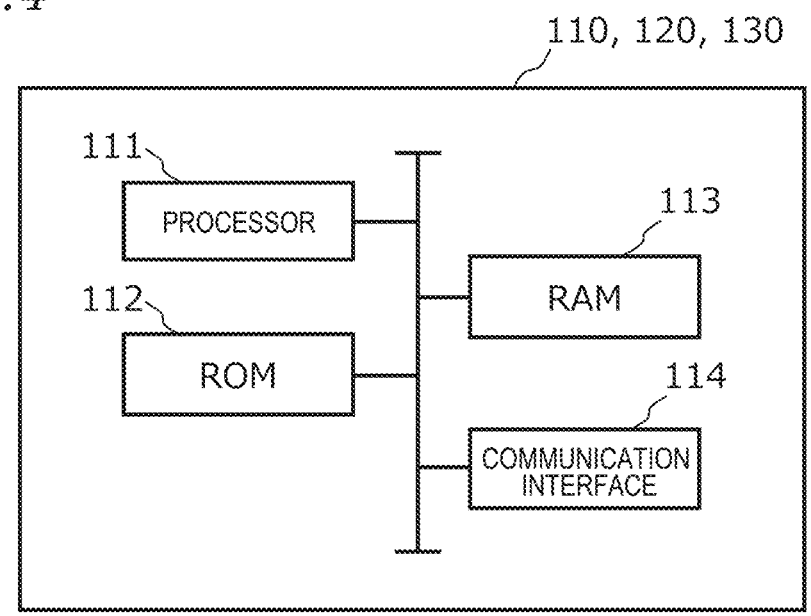
FIG. 4 is a block diagram showing an example of hardware configuration of a first controller 110, a second controller 120 and a third controller 130 according to a preferred embodiment of the present invention.

FIG. 4 is a block diagram showing an example of hardware configuration of the first controller 110, the second controller 120 and the third controller 130.

The first controller 110, the second controller 120 and the third controller 130 each include a processor 111, and storage mediums such as, for example, a ROM (Read Only Memory) 112 and a RAM (Random Access Memory) 113. The ROM 112 has a computer program (or firmware) stored thereon that causes the processor 111 to execute processes. The computer program may be supplied to the drive unit 10 via a storage medium (e.g., a semiconductor memory) or an electric communication line (e.g., the Internet). Such a computer program may be marketed as commercial software.

The processor 111 is, for example, a semiconductor integrated circuit and includes, for example, a central processing unit (CPU). The processor 111 may include a microprocessor or a microcontroller. The processor 111 sequentially executes computer programs (computer programs stored on the ROM 112) describing a group of instructions provided to execute various processes, and thus executes a desired process.

The processor 111 may be an FPGA (Field Programmable Gate Array), a GPU (Graphics Processing Unit), an ASIC (Application Specific Integrated Circuit) or an ASSP (Application Specific Standard Product) each having a CPU mounted thereon, or a combination of two or more circuits selected from these circuits.

The ROM 112 is, for example, a writable memory (e.g., a PROM), a rewritable memory (e.g., a flash memory), or a read-only memory. The ROM 112 does not need to be a single storage medium, and may be an assembly of a plurality of storage mediums. The RAM 113 provides a work area where the computer program stored on the ROM 112 is once developed at the time of booting. The RAM 113 does not need to be a single storage medium, and may be an assembly of a plurality of storage mediums. A communication IF 114 is a communication module to communicate with an external device. The communication IF 114 may provide wired and/or wireless communication.

The torque sensor 50L (FIG. 3) detects a torque applied by the user to the hand rim 3L. The torque sensor 50R (FIG. 3) detects a torque applied by the user to the hand rim 3R.

The rim base 31 (FIG. 1) is displaceable in a rotation direction thereof with respect to the wheel hub 21. An elastic member is provided between the wheel hub 21 and the rim base 31. The elastic member pressurizes the rim base 31 such that the rim base 31 is kept at a neutral position in the positional relationship between the wheel hub 21 and the rim base 31. The torques applied by the user to the hand rims 3L and 3R are transmitted to the rim bases 31 via the plurality of connection pipes 32. When the torque applied to each of the rim bases 31 exceeds the pressure applied by the elastic member, the rim base 31 is displaced with respect to the wheel hub 21 against the elastic force of the elastic member.

Figure 5:
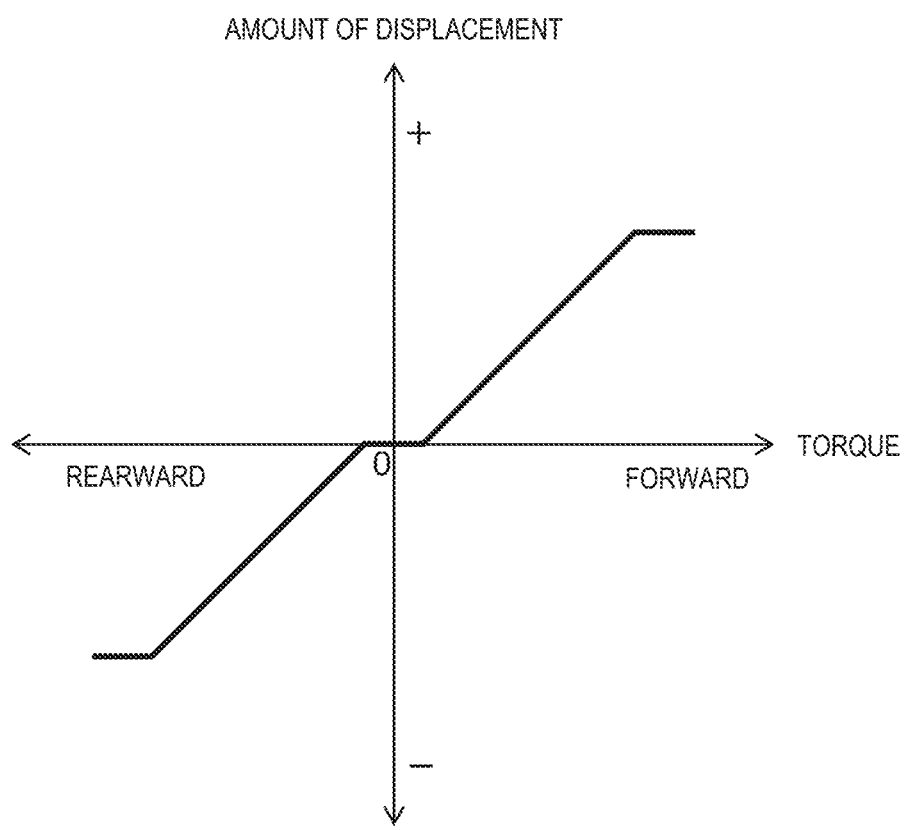
FIG. 5 shows an example of a relationship between the torque applied to a rim base 31 and the amount of displacement of the rim base 31 with respect to a wheel hub 21 according to a preferred embodiment of the present invention.

FIG. 5 shows an example of a relationship between the torque applied to the rim base 31 and the amount of displacement of the rim base 31 with respect to the wheel hub 21. The vertical axis represents the amount of displacement of the rim base 31 with respect to the wheel hub 21. The horizontal axis represents the torque applied to the rim base 31.

In a state where no torque is applied to the rim base 31, the rim base 31 is at the neutral position, and the amount of displacement is zero. When a torque in a direction of moving the vehicle forward is applied to the rim base 31 and the torque exceeds the pressure applied by the elastic member, the rim base 31 is displaced with respect to the wheel hub 21 against the elastic force of the elastic member. In FIG. 5, this displacement is shown as a displacement in a positive direction. As the torque increases, the amount of displacement increases in the positive direction. A stopper that restricts the range of displacement is provided between the wheel hub 21 and the rim base 31. When the amount of displacement reaches a predetermined level, the stopper stops the displacement of the rim base 31 with respect to the wheel hub 21.

When a torque in a direction of moving the vehicle rearward is applied to the rim base 31 and the torque exceeds the pressure applied by the elastic member, the rim base 31 is displaced with respect to the wheel hub 21 against the elastic force of the elastic member. In FIG. 5, this displacement is shown as a displacement in a negative direction. As the torque increases, the amount of displacement increases in the negative direction. When the amount of displacement reaches a predetermined level, the stopper stops the displacement of the rim base 31 with respect to the wheel hub 21.

The torque sensors 50L and 50R (FIG. 3) may each be a displacement sensor that detects an amount of such a relative displacement of the rim base 31 and the wheel hub 21. The relationship between the torque and the amount of displacement is known in advance. Therefore, the torque may be detected by detecting the amount of displacement.

The torque sensors 50L and 50R may each be, for example, a potentiometer or a magnetic sensor. In the case where the torque sensors 50L and 50R are each a magnetic sensor, the amount of displacement may be detected because the positional relationship between the magnetic sensor and a magnet is changed in accordance with the relative displacement of the rim base 31 and the wheel hub 21. Alternatively, a ferromagnetic member may be located between the magnetic sensor and the magnet, so that the amount of displacement is detected in accordance with a change in the positional relationship between the magnetic sensor and the ferromagnetic member. A magnetostrictive torque sensor may be used as each of the torque sensors 50L and 50R. The torque sensors 50L and 50R each output a signal in accordance with the detected torque (detected amount of displacement) to the first controller 110, the second controller 120 and the third controller 130.

As shown in FIG. 3, the electric motor 25L is provided with the speed sensor 26L. The electric motor 25R is provided with the speed sensor 26R. The speed sensors 26L and 26R are each, for example, an encoder.

The speed sensor 26L detects a rotation angle of the rotor of the electric motor 25L and outputs a signal in accordance with the rotation angle to the first controller 110 and the second controller 120. The first controller 110 and the second controller 120 each calculate the rotation speed of the electric motor 25L based on the output signal from the speed sensor 26L.

The speed sensor 26R detects a rotation angle of the rotor of the electric motor 25R and outputs a signal in accordance with the rotation angle to the first controller 110 and the third controller 130. The first controller 110 and the third controller 130 each calculate the rotation speed of the electric motor 25R based on the output signal from the speed sensor 26R.

The size of the tires of the wheels 2L and 2R is known in advance. Thus, the first controller 110, the second controller 120 and the third controller 130 may calculate the running speed of the electrically assisted wheelchair 1 based on the rotation speeds of the electric motors 25L and 25R. In the case where the rotations of the electric motors 25L and 25R are transmitted to the wheels 2L and 2R via the decelerators, the running speed of the electrically assisted wheelchair 1 is calculated further based on information on deceleration ratios of the decelerators.

The speed sensors 26L and 26R may respectively be provided in the wheel hubs 21 (FIG. 1), the outer circumferential portions 23 or the spokes 22 of the wheels 2L and 2R. The speed sensors 26L and 26R may respectively output signals in accordance with rotations of the members in which the speed sensors 26L and 26R are provided.

The drive unit 10 causes the electric motors 25L and 25R to generate driving power in accordance with the human power applied by the user on the hand rims 3L and 3R.

The second controller 120 uses the output signal from the torque sensor 50L to calculate the torque transmitted from the hand rim 3L to the wheel 2L. The second controller 120 calculates a command value to generate an appropriate torque, based on the calculated torque, the running speed of the electrically assisted wheelchair 1 and the like. The second controller 120, for example, refers to a map created based on, for example, the relationship between the torque transmitted from the hand rim 3L to the wheel 2L and the torque generated by the electric motor 25L to calculate the command value. The ROM 112 (FIG. 4) has a plurality of types of maps stored thereon. The second controller 120 reads the map suitable to conditions from the ROM 112 and refers to the read map to calculate the command value.

The second controller 120 outputs the calculated command value to the addition circuit 140L. The addition circuit 140L outputs a command value that is a sum of the command value output from the second controller 120 and a command value output from the first controller 110 to the driving circuit 150L. In the case where no command value is output from the first controller 110, the command value output from the second controller 120 is input to the driving circuit 150L.

The third controller 130 uses the output signal from the torque sensor 50R to calculate the torque transmitted from the hand rim 3R to the wheel 2R. The third controller 130 calculates a command value to generate an appropriate torque, based on the calculated torque, the running speed of the electrically assisted wheelchair 1 and the like. The third controller 130, for example, refers to a map to calculate the command value in the same manner as the second controller 120.

The third controller 130 outputs the calculated command value to the addition circuit 140R. The addition circuit 140R outputs a command value that is a sum of the command value output from the third controller 130 and the command value output from the first controller 110 to the driving circuit 150R. In the case where no command value is output from the first controller 110, the command value output from the third controller 130 is input to the driving circuit 150R. The driving circuits 150L and 150R each include, for example, an inverter. The driving circuit 150L generates a driving current in accordance with the command value and supplies the driving current to the electric motor 25L. The driving circuit 150R generates a driving current in accordance with the command value and supplies the driving current to the electric motor 25R. The electric motors 25L and 25R supplied with the driving currents each rotate to generate a predetermined torque.

As described above, the second controller 120 and the third controller 130 cause the electric motors 25L and 25R to generate torques so as to assist a motion of the user pushing the hand rims 3L and 3R. The torques applied by the user to the hand rims 3L and 3R and the torques generated by the electric motors 25L and 25R are transmitted to the wheels 2L and 2R, and as a result, the electrically assisted wheelchair 1 runs. Since the electric motors 25L and 25R each generate a torque, the load imposed on the user pushing the hand rims 3L and 3R may be alleviated.

Figure 6:
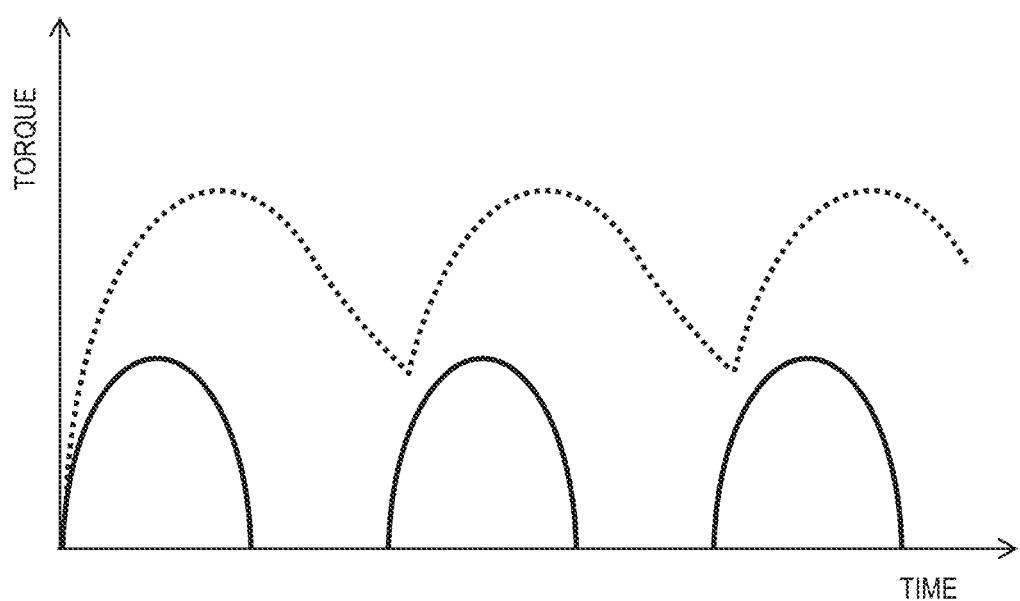
FIG. 6 shows an example of a waveform of a torque applied by a user to each of hand rims 3L and 3R and an example of a waveform of a torque generated by each of electric motors 25L and 25R according to a preferred embodiment of the present invention.

FIG. 6 shows an example of a waveform of the torque applied by the user to each of the hand rims 3L and 3R and an example of a waveform of the torque generated by each of the electric motors 25L and 25R. The vertical axis represents the torque, and the horizontal axis represents the time. In FIG. 6, the solid line represents the torque applied by the user to each of the hand rims 3L and 3R, and the dotted line represents the torque generated by each of the electric motors 25L and 25R.

The electric motors 25L and 25R are controlled such that even when the torque applied by the user is zero, the torque generated by each of the electric motors 25L and 25R is not zero immediately but is gradually decreased.

The operation, made by the user, of pushing the hand rims 3L and 3R is made intermittently. After the user takes his/her hand off from the hand rim 3L or 3R but before he/she grips the hand rim 3L or 3R again, the electrically assisted wheelchair 1 runs by inertia. However, when on an upslope or the like, the electrically assisted wheelchair 1 may possibly be decelerated significantly while no human power is applied to the hand rim 3L or 3R. The torque generated by each of the electric motors 25L and 25R is gradually decreased, and therefore, the electrically assisted wheelchair 1 may be suppressed from being decelerated even while no human power is applied to the hand rim 3L or 3R. Such an arrangement also allows the electrically assisted wheelchair 1 to run more smoothly on a flat road.

The drive unit 10 may be detachable from the vehicle frame 4 of the electrically assisted wheelchair 1. The drive unit 10 may be detachable from a vehicle frame different from the vehicle frame 4. For example, a wheel may be detached from a vehicle frame of a common wheelchair and the drive unit 10 may be attached to the vehicle frame, so that the common wheelchair is usable as the electrically assisted wheelchair 1.

The drive unit 10 includes the two controllers 120 and 130 respectively controlling the electric motors 25L and 25R. The drive unit 10 is not limited to having such a structure, and may include one controller controlling both of the electric motors 25L and 25R. Alternatively, the processes executed by the controllers 110, 120 and 130 may be performed by one controller.

The drive unit 10 does not need to include any of the wheels 2L and 2R and the hand rims 3L and 3R. In the case of including none of these, the drive unit 10 is attached to a wheelchair including wheels and hand rims.

Now, control of the electrically assisted wheelchair 1 in a cruise control mode will be described.

The drive unit 10 may cause the electric motors 25L and 25R to generate torques to execute a cruise control by which the electrically assisted wheelchair 1 runs while keeping the running speed at the target speed. In this preferred embodiment, the cruise control is started in the case where the user applies power to each of the hand rims 3L and 3R continuously for a predetermined time period.

Figure 7:
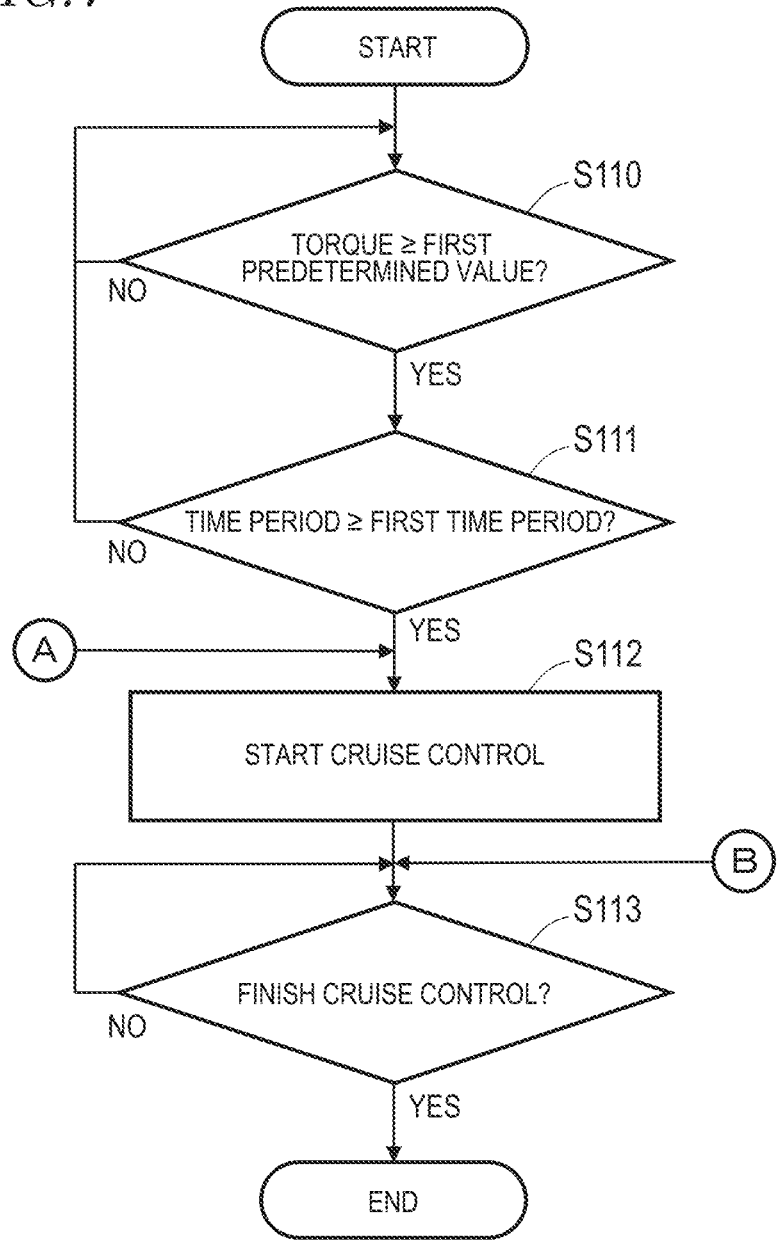
FIG. 7 is a flowchart showing a process of starting a cruise control according to a preferred embodiment of the present invention.

FIG. 7 is a flowchart showing a process of starting the cruise control.

To the first controller 110 (FIG. 3), the output signals from the torque sensors 50L and 50R and the output signals from the speed sensors 26L and 26R are input. The first controller 110 calculates the running speed of the electrically assisted wheelchair 1 based on the output signals from the speed sensors 26L and 26R.

The first controller 110 uses the output signals from the torque sensors 50L and 50R to detect forward-direction torques respectively applied to the hand rims 3L and 3R. Upon detecting such torques, the first controller 110 determines whether or not the torques each have a value no smaller than a first predetermined value Tr1 (step S110). The "forward-direction torques applied to the hand rims 3L and 3R" are each a torque in a direction of moving the vehicle forward. The first predetermined value Tr1 may be any value. The first predetermined value Tr1 may be, for example, a value at which the torque sensors 50L and 50R start detecting the displacement shown in FIG. 5, or a larger value.

Upon determining that the torques each have a value no smaller than the first predetermined value Tr1, the first controller 110 measures a time period in which a first state continues. The first state is a state where the output signals from the torque sensors 50L and 50R indicate that the torques each have a value no smaller than the first predetermined value Tr1. The first controller 110 determines whether or not the time period in which the first state continues is no shorter than a first time period t1 (step S111). The first time period t1 is, for example, about 0.1 to about 0.2 seconds, but is not limited to such a length.

In the case where before the first time period t1 elapses, the value of at least one of the torques applied to the hand rims 3L and 3R becomes smaller than the first predetermined value Tr1, the measurement of the time period is finished, and the process of step S110 is repeated.

Upon determining that the time period in which the first state continues is no shorter than the first time period t1, the first controller 110 starts controlling the electric motors 25L and 25R in the cruise control mode, by which the electrically assisted wheelchair 1 runs while keeping the running speed at the target speed (step S112).

The target speed is preset and is stored on the ROM 112 (FIG. 4).

In the cruise control mode, the first controller 110 calculates a command value to cause the electric motors 25L and 25R to generate an appropriate torque. The first controller 110 executes, for example, PID control (Proportional-Integral-Derivative Control). In the case where the running speed of the electrically assisted wheelchair 1 is lower than the target speed, the first controller 110 calculates a command value to increase the running speed. In the case where the running speed of the electrically assisted wheelchair 1 is higher than the target speed, the first controller 110 calculates a command value to decrease the running speed. In the case where the running speed of the electrically assisted wheelchair 1 matches the target speed, the first controller 110 calculates a command value to keep the running speed.

The first controller 110 outputs the calculated command value to the addition circuits 140L and 140R. The addition circuit 140L outputs a command value that is a sum of the command value output from the first controller 110 and the command value output from the second controller 120 to the driving circuit 150L. In the case where no command value is output from the second controller 120, the command value output from the first controller 110 is input to the driving circuit 150L.

The addition circuit 140R outputs a command value that is a sum of the command value output from the first controller 110 and the command value output from the third controller 130 to the driving circuit 150R. In the case where no command value is output from the third controller 130, the command value output from the first controller 110 is input to the driving circuit 150R.

The driving circuit 150L generates a driving current in accordance with the command value and supplies the driving current to the electric motor 25L. The driving circuit 150R generates a driving current in accordance with the command value and supplies the driving current to the electric motor 25R. The electric motors 25L and 25R supplied with the driving currents each rotate, and as a result, the electrically assisted wheelchair 1 runs while keeping the running speed at the target speed.

In this preferred embodiment, the electrically assisted wheelchair 1 may start running in the cruise control mode by a simple operation, made by the user, of applying power to the hand rims 3L and 3R for a certain time period. The user does not need to make any special operation to start running the electrically assisted wheelchair 1 in the cruise control mode. Therefore, the convenience for the user may be improved.

Since the target speed is preset, the electrically assisted wheelchair 1 may run at the same speed each time while the control in the cruise control mode is executed. Even in the case where it is difficult to increase the running speed in accordance with the motion of the user pushing the hand rims 3L and 3R, for example, even in the case where the electrically assisted wheelchair 1 is on an upslope, the running speed is increased to the preset target speed by the cruise control. Therefore, the electrically assisted wheelchair 1 may run at the speed intended by the user.

In the case where conditions to finish the cruise control mode are fulfilled, the first controller 110 finishes the cruise control mode (step S113). For example, as described below, in the case where the user performs an operation of applying power to the hand rims 3L and 3R in a rearward direction for a certain time period, the first controller 110 finishes the cruise control mode.

The first controller 110 may start the control in the cruise control mode in the case where the time period in which either one of the forward-direction torque applied to the hand rim 3L and the forward-direction torque applied to the hand rim 3R has a value no smaller than the first predetermined value Tr1 continues for the first time period t1. The cruise control may be started by an operation made by one hand of the user. This may improve the convenience for the user.

In the case where the running speed of the electrically assisted wheelchair 1 is low, the control of the electric motor 25L or 25R in the cruise control mode does not need to be started. If the cruise control mode is turned on while the electrically assisted wheelchair 1 runs at a low speed in a small area, for example, indoors, the user may possibly feel uneasy. Since the cruise control mode may be set not to be turned on while the running speed is low, the convenience for the user may be improved.

In this case, if the running speed is, for example, lower than a first speed, the first controller 110 does not start the control in the cruise control mode. The first speed is, for example, about 1.0 km/h, but is not limited to this. The first controller 110 starts the control in the cruise control mode in the case where the running speed is the first speed or higher and the measured time period is the first time period t1 or longer.

Now, a process in which no target speed is set will be described.

Figure 8:
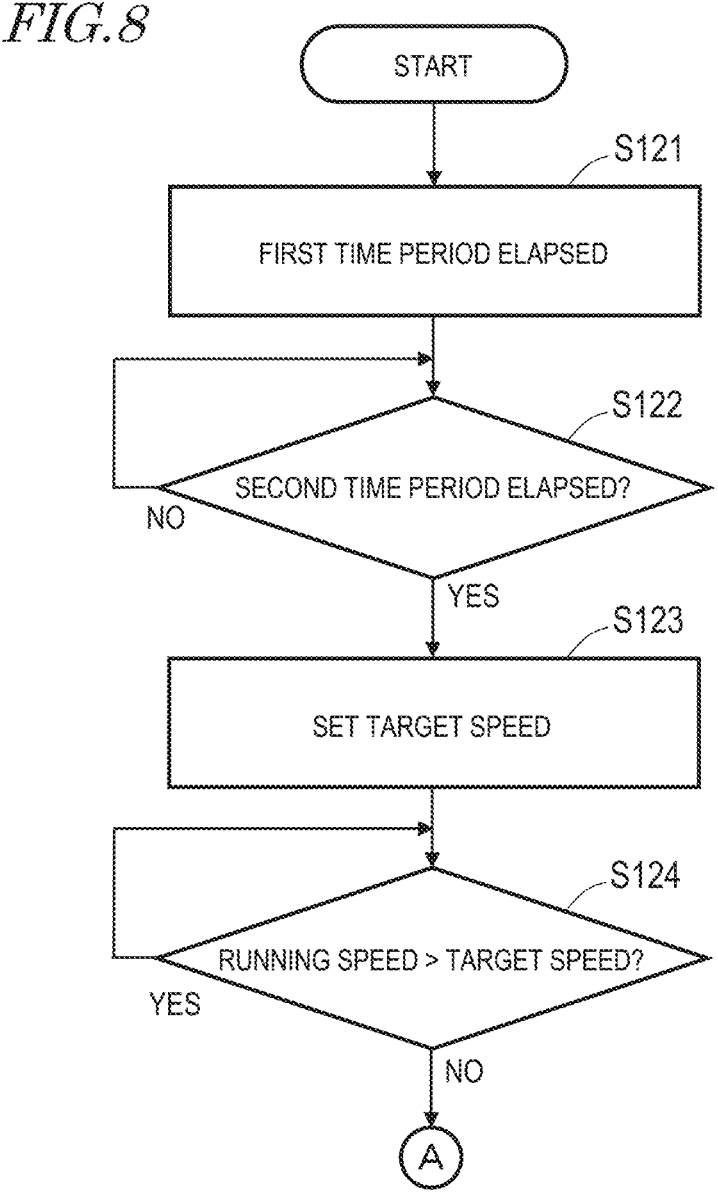
FIG. 8 is a flowchart showing a process of setting a target speed according to a preferred embodiment of the present invention.

FIG. 8 is a flowchart showing a process of setting the target speed in which no target speed is preset.

In the case where the time period in which the first state continues is the first time period t1, the first controller 110 keeps measuring the time period (step S121). As described above, the first state is a state where the output signals from the torque sensors 50L and 50R indicate that the torques each have a value no smaller than the first predetermined value Tr1.

The first controller determines whether or not a second time period t2 has elapsed after the measured time reached the first time period t1 (step S122). The second time period t2 is, for example, about 0.2 to about 0.5 seconds, but is not limited to such a length.

Upon determining that the second time period t2 has elapsed, the first controller 110 sets, as the target speed, the running speed of the electrically assisted wheelchair 1 at the time when the second time period t2 elapsed (step S123).

The first controller 110 determines whether or not the running speed after the target speed is set is higher than the target speed (step S124). In the case where, for example, the running speed keeps increasing after the second time period t2 elapses, the running speed is higher than the target speed. In this case, the control of keeping the running speed at the target speed is started at the time when the running speed is decreased to the target speed. Upon determining that the running speed is the target speed or lower, the first controller 110 advances to the process of step S112 in FIG. 7, and starts the control of keeping the running speed at the target speed (control in the cruise control mode).

Since the running speed at the time when the second time period t2 elapses is set as the target speed, the running speed obtained as a result of acceleration performed during the second time period t2 may be set as the target speed. Therefore, the target speed may reflect the user's intention to increase the running speed by pushing the hand rims 3L and 3R.

The user may finish the motion of continuously applying the power to the hand rims 3L and 3R after applying the power to the hand rims 3L and 3R for the first time period t1 but before the second time period t2 elapses. Alternatively, the user may apply the power to the hand rims 3L and 3R for the first time period t1 and further until the second time period t2 elapses. In either case, the running speed at the time when the second time period t2 elapses is set as the target speed. Therefore, the target speed may reflect the user's intention.

After the second time period t2 elapses, the electrically assisted wheelchair 1 is further accelerated. Then, the electrically assisted wheelchair 1 is mildly decelerated. During the mild deceleration, the control of keeping the running speed at the target speed is started. In this manner, the deviation of the actual change in speed from the change in speed imagined by the user operating the electrically assisted wheelchair 1 may be reduced.

Even when the target speed is preset, in the case where the running speed keeps increasing after the first time period t1 elapses and becomes higher than the target speed, the control of keeping the running speed at the target speed may be started at the time when the running speed is decreased to the target speed. After the first time period t1 elapses, the electrically assisted wheelchair 1 is further accelerated. Then, the electrically assisted wheelchair 1 is mildly decelerated. During the mild deceleration, the control of keeping the running speed at the target speed is started. In this manner, the deviation of the actual change in speed from the change in speed imagined by the user operating the electrically assisted wheelchair 1 may be reduced.

In the case where the running speed at the time when the first time period t1 elapses is lower than the preset target speed, the first controller 110 controls the electric motors 25L and 25R so as to match the running speed to the target speed, and then executes the control of keeping the running speed at the target speed. This makes it unnecessary for the user to make an additional motion of increasing the running speed to the target speed, and thus may improve the convenience for the user.

Now, control of changing the running speed in accordance with the operation made by the user during the execution of the cruise control will be described.

As described above, the second controller 120 and the third controller 130 execute assist control of causing the electric motors 25L and 25R to generate torques so as to assist the motion of the user pushing the hand rims 3L and 3R. The assist control may be executed during the control of keeping the running speed at the target speed.

In the case where, for example, during the control of keeping the running speed at the target speed, the output signals from the torque sensors 50L and 50R indicate that the forward-direction torques applied to the hand rims 3L and 3R each have a value no smaller than the first predetermined value Tr1, the second controller 120 and the third controller 130 respectively calculate command values in accordance with the levels of the output signals from the torque sensors 50L and 50R. The second controller 120 and the third controller 130 respectively output the calculated command values to the addition circuits 140L and 140R.

The addition circuit 140L outputs a command value that is a sum of the command value output from the first controller 110 and the command value output from the second controller 120 to the driving circuit 150L. The addition circuit 140R outputs a command value that is a sum of the command value output from the first controller 110 and the command value output from the third controller 130 to the driving circuit 150R.

The driving circuit 150L generates a driving current in accordance with the command value and supplies the driving current to the electric motor 25L. The driving circuit 150R generates a driving current in accordance with the command value and supplies the driving current to the electric motor 25R. The electric motors 25L and 25R supplied with the driving currents each generate a torque having a value that is a sum of the torque to keep the running speed at the target speed and the torque in accordance with the level of the output signal from the torque sensor 50L or 50R.

Even during the execution of the cruise control, the running speed may be changed in accordance with the operation, made by the user, of pushing the hand rims 3L and 3R. Therefore, the electrically assisted wheelchair 1 may run as intended by the user. The rotation rate of one of the wheels 2L and 2R may be changed in accordance with the operation made by the user to the corresponding hand rim 3L or 3R. Therefore, the advancing direction of the electrically assisted wheelchair 1 may be changed during the execution of the cruise control.

Now, a process of changing the target speed in accordance with the operation made by the user during the execution of the cruise control will be described.

Figure 9:
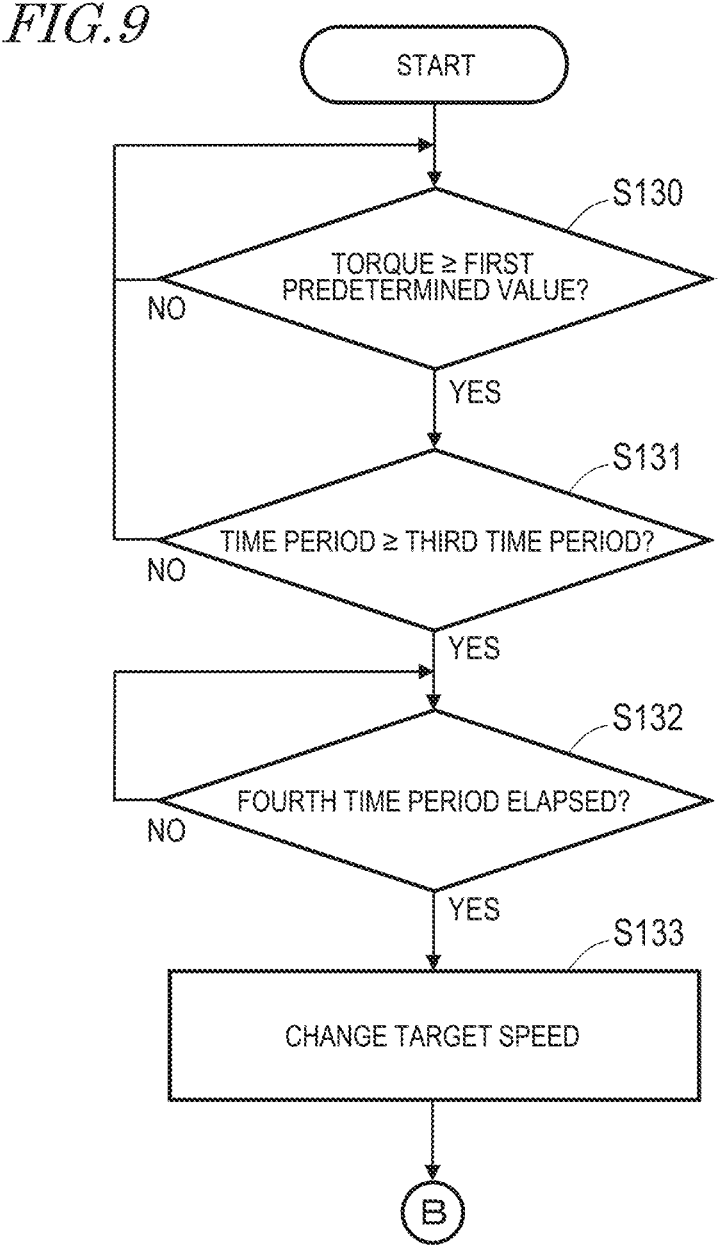
FIG. 9 is a flowchart showing a process of changing the target speed in accordance with an operation made by a user during the execution of the cruise control according to a preferred embodiment of the present invention.

FIG. 9 is a flowchart showing a process of changing the target speed in accordance with the operation made by the user during the execution of the cruise control.

Upon detecting forward-direction torques applied to the hand rims 3L and 3R during the execution of the cruise control, the first controller 110 determines whether or not the torques each have a value no smaller than the first predetermined value Tr1 (step S130).

Upon determining that the torques each have a value no smaller than the first predetermined value Tr1, the first controller 110 measures the time period in which the first state, where the output signals from the torque sensors 50L and 50R indicate that the torques each have a value no smaller than the first predetermined value Tr1, continues. The first controller 110 determines whether or not the time period in which the first state continues is no shorter than a third time period t3 (step S131). The third time period t3 is, for example, about 0.1 to about 0.2 seconds, but is not limited to such a length.

In the case where before the third time period t3 elapses, the value of at least one of the torques applied to the hand rims 3L and 3R becomes smaller than the first predetermined value Tr1, the measurement of the time period is finished, and the process of step S130 is repeated.

Upon determining that the time period in which the first state continues is no shorter than the third time period t3, the first controller 110 keeps measuring the time period. The first controller 110 determines whether or not a fourth time period t4 has elapsed after the measured time reached the third time period t3 (step S132). The fourth time period t4 is, for example, about 0.2 to about 0.5 seconds, but is not limited to such a length.

Upon determining that the fourth time period t4 has elapsed, the first controller 110 changes the target speed to the running speed of the electrically assisted wheelchair 1 at the time when the fourth time period t4 elapsed (step S133). The first controller 110 executes the control of keeping the running speed at the post-change target speed.

Since the target speed is changed in accordance with the operation made by the user, the electrically assisted wheelchair 1 may run in a manner reflecting the user's intention to increase the running speed to be kept in the cruise control.

Now, a process of finishing the control in the cruise control mode will be described. In this preferred embodiment, in the case where the user performs an operation of applying power to the hand rims 3L and 3R in the rearward direction for a certain time period, the cruise control mode is finished.

Figure 10:
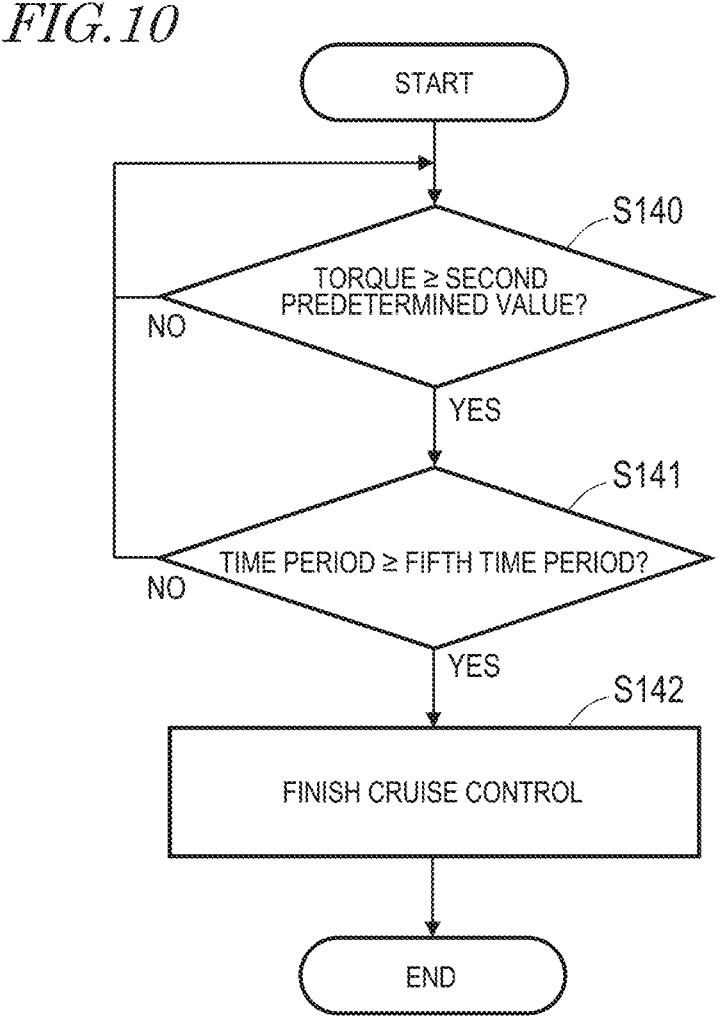
FIG. 10 is a flowchart showing a process of finishing a cruise control mode according to a preferred embodiment of the present invention.

FIG. 10 is a flowchart showing a process of finishing the cruise control mode.

The first controller 110 uses the output signals from the torque sensors 50L and 50R to detect rearward-direction torques applied to the hand rims 3L and 3R. Upon detecting such torques, the first controller 110 determines whether or not the torques each have a value no smaller than a second predetermined value Tr2 (step S140). The "rearward-direction torques applied to the hand rims 3L and 3R" are each a torque in a direction of moving the vehicle rearward. A torque generated when the user grips the hand rims 3L and 3R so as to brake the wheels 2L and 2R rotating forward is also encompassed in the rearward-direction torque. The second predetermined value Tr2 may be any value. The second predetermined value Tr2 may be, for example, a value at which the torque sensors 50L and 50R start detecting the displacement shown in FIG. 5, or a larger value.

Upon determining that the torques each have a value no smaller than the second predetermined value Tr2, the first controller 110 measures a time period in which a second state continues. The second state is a state where the output signals from the torque sensors 50L and 50R indicate that the torques each have a value no smaller than the second predetermined value Tr2. The first controller 110 determines whether or not the time period in which the second state continues is no shorter than a fifth time period t5 (step S141). The fifth time period t5 is, for example, about 0.1 to about 0.2 seconds, but is not limited to such a length.

In the case where before the fifth time period t5 elapses, the value of at least one of the torques applied to the hand rims 3L and 3R becomes smaller than the second predetermined value Tr2, the measurement of the time period is finished, and the process of step S140 is repeated.

Upon determining that the time period in which the second state continues is no shorter than the fifth time period t5, the first controller 110 finishes the control of the electric motors 25L and 25R in the cruise control mode (step S142).

The user may finish the cruise control mode by a simple operation of applying power to the hand rims 3L and 3R in the rearward direction for a certain time period. This may improve the convenience for the user.

In general, for significantly changing the advancing direction of, or stopping, the electrically assisted wheelchair 1, the user may make an operation of applying power to the hand rims 3L and 3R in the rearward direction. In the same manner of operation as this, the user may finish the cruise control mode in the same manner. Therefore, the user may operate the electrically assisted wheelchair 1 by substantially the same sense as for a conventional wheelchair.

The control in the cruise control mode may be finished in the case where the time period in which either one of the rearward-direction torque applied to the hand rim 3L and the rearward-direction torque applied to the hand rim 3R has a value no smaller than the second predetermined value Tr2 continues for the fifth time period t5. The cruise control may be finished by an operation made by one hand of the user. This may improve the convenience for the user.

In accordance with an operation made by the user to one of the hand rims 3L and 3R in the rearward direction, the control in the cruise control mode may be finished on the corresponding side. In this case, the advancing direction of the electrically assisted wheelchair 1 may be changed easily.

The cruise control mode may be finished in the case where the running speed of the electrically assisted wheelchair 1 is decreased. For example, in the case where the running speed is decreased to a speed no higher than a second speed, which is lower than the target speed, during the control of keeping the running speed at the target speed, the first controller 110 finishes the control in the cruise control mode. The second speed is, for example, about 50% to about 60% of the target speed, but is not limited to such a speed.

In the case where it becomes difficult to keep the target speed merely by the driving power generated by the electric motors 25L and 25R, for example, in the case where the electrically assisted wheelchair 1 is on an upslope having a large inclining angle, the cruise control mode may be finished and the electrically assisted wheelchair 1 may be run by power that is a sum of the human power and the driving power provided by the electric motors 25L and 25R. In this manner, the electrically assisted wheelchair 1 may keep running.

In the case where a state where the electric motors 25L and 25R are caused to generate large driving power continues for a certain time period, the cruise control mode may be finished. For example, the first controller 110 finishes the control in the cruise control mode in the case where a state where a command value to drive the electric motors 25L and 25R is a threshold value or larger continues for a sixth time period t6. The sixth time period t6 is, for example, about 2.0 to about 3.0 seconds, but is not limited to such a length.

In the case where a state where the electric motors 25L and 25R are caused to generate large driving power continues for a certain time period, the cruise control mode may be finished and the electrically assisted wheelchair 1 may be run by power that is a sum of the human power and the driving power provided by the electric motors 25L and 25R. This allows the electrically assisted wheelchair 1 to keep running while the running speed is suppressed from being decreased.

The control in the cruise control mode may be finished in the case where the battery 7 has a remaining capacity smaller than a threshold value. In the case where the remaining capacity of the battery 7 is small, the control in the cruise control mode does not need to be executed. This may suppress the power consumption.

Now, settings on a motion of the drive unit 10 by an external device will be described.

FIG. 11 shows the electrically assisted wheelchair 1 and an external device 200. The external device 200 is, for example, a personal computer (PC), a tablet computer, a smartphone, or a PDA (Personal Digital Assistant). In FIG. 11, a laptop PC and a tablet computer are shown as examples of the external device 200.

The controller 100 (FIG. 3) of the electrically assisted wheelchair 1 may perform wired and/or wireless communication with the external device 200. The controller 100 uses, for example, the communication IF 114 (FIG. 4) to communicate with the external device 200. The controller 100 may include another communication IF different from the communication IF 114 and use the another communication IF to communicate with the external device 200.

For example, the external device 200 transmits, to the controller 100, setting information on whether or not the execution of the control in the cruise control mode is permissible. In the case where the setting information indicates that the execution of the control in the cruise control mode is permissible, the first controller 110 of the controller 100 executes the control in the cruise control mode. In this case, the first controller 110 starts the control in the cruise control mode in the case where the time period in which the first state described above with reference to FIG. 7 continues is the first time period t1 or longer. In the case where the setting information prohibits the execution of the control in the cruise control mode, the first controller 110 does not execute the control in the cruise control mode.

As described above, the external device 200 may set whether or not the execution of the control in the cruise control mode is permissible. For example, while the electrically assisted wheelchair 1 is in an area that is not suitable to running in the cruise control mode, the external device 200 transmits, to the controller 100, setting information that prohibits the execution of the control in the cruise control mode. In this manner, the electrically assisted wheelchair 1 may run appropriately in the area.

The external device 200 may transmit target speed information indicating the target speed to the controller 100. In this case, the first controller 110 sets a value indicated by the target speed information as the target speed.

Since the external device 200 sets the target speed, the user sitting on the electrically assisted wheelchair 1 does not need to set the target speed. This may improve the convenience for the user.

The external device 200 may transmit, to the drive unit 10, target speed information indicating a target speed varying in accordance with the area in which the electrically assisted wheelchair 1 runs. In this case, the electrically assisted wheelchair 1 may run at the running speed suitable to the area where the electrically assisted wheelchair 1 is running.

Now, the notification device 8 that notifies the user of the state of the electrically assisted wheelchair 1 will be described.

Figure 12:
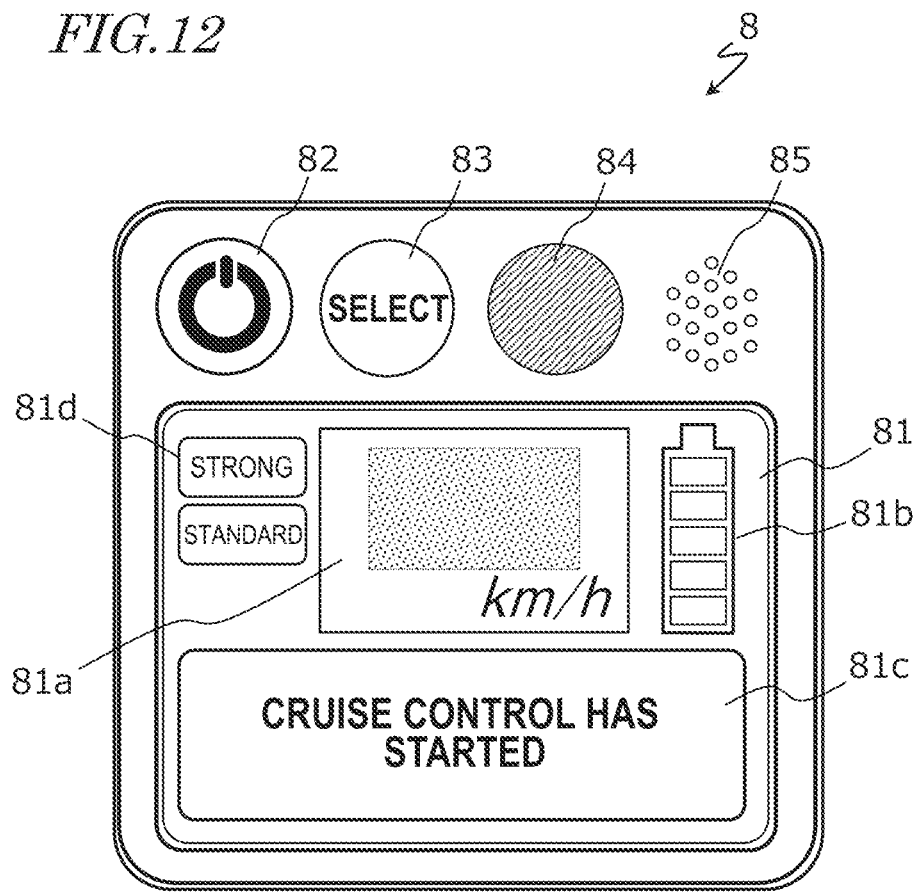
FIG. 12 shows an example of a notification device 8 according to a preferred embodiment of the present invention.

FIG. 12 shows an example of the notification device 8. The notification device 8 is provided on, for example, one of the arm rests 42 (FIG. 1). The notification device 8 includes a display 81, a power switch 82, a selection switch 83, a lamp 84, and a speaker 85.

The display 81 is, for example, a liquid crystal panel or an organic EL panel. The display 81 may display by a segment system or a dot matrix system. The display 81 includes a speed display area 81a, a battery remaining capacity display area 81b, a notification area 81c, and an assist mode display area 81d.

The speed display area 81a displays the running speed of the electrically assisted wheelchair 1 with a numerical figure(s). The battery remaining capacity display area 81b displays the remaining capacity of the battery 7 with a segment(s). This allows the user to learn the remaining capacity of the battery 7 intuitively. The assist mode display area 81d displays the assist mode selected by the user operating the selection switch 83. The assist mode is, for example, a "strong mode" or a "standard mode".

The notification area 81c displays various information to be notified to the user. When, for example, the control in the cruise control mode has been started, the notification area 81c displays information indicating that the cruise control has been started. When the control in the cruise control mode has been finished, the notification area 81c displays information indicating that the cruise control has been finished. While the control in the cruise control mode is being executed, the notification area 81c displays information indicating that the cruise control is being executed. This allows the user to recognize that the cruise control has been started, is being executed, or has been finished.

The lamp 84 may be lit up to notify the user that the cruise control has been started, is being executed, or has been finished. For example, the color of the lamp 84 may be varied to notify the user of such information. Alternatively, the speaker 85 may output an audio signal to notify the user of such information.

Figure 13:
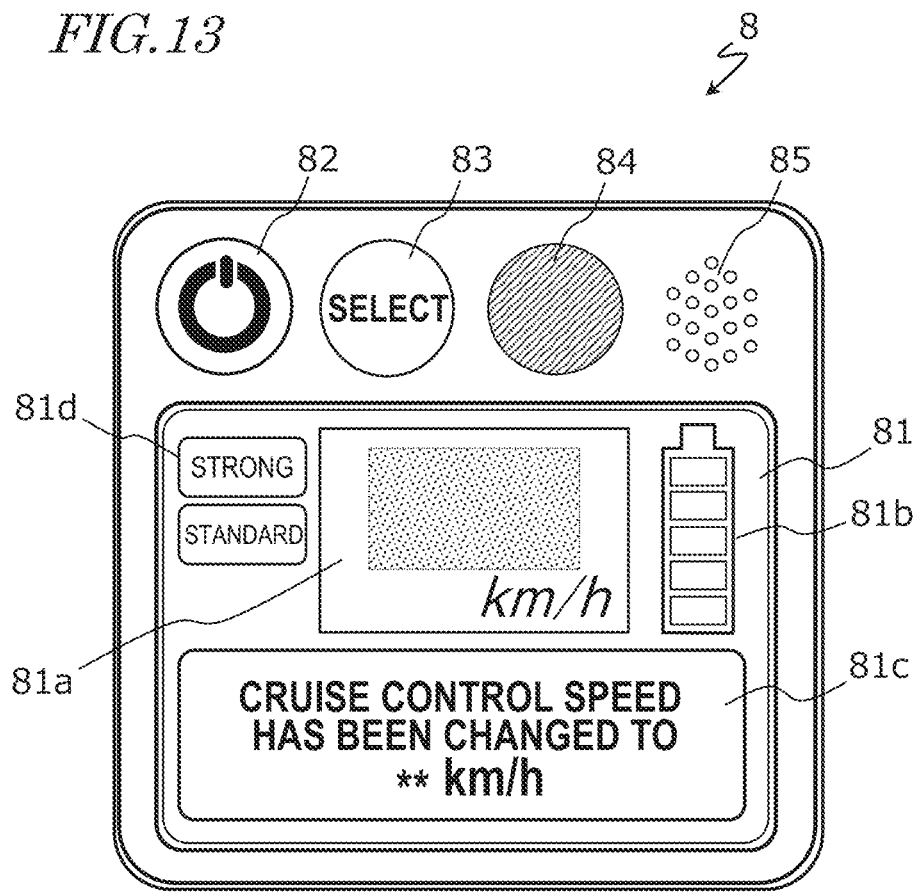
FIG. 13 shows an example of information displayed by the notification device 8 according to a preferred embodiment of the present invention.

In the case where the target speed has been changed, the notification area 81c may display information indicating that the target speed has been changed. FIG. 13 shows an example of the notification area 81c displaying information indicating that the target speed has been changed. This allows the user to recognize that the target speed has been changed. The lamp 84 may be lit up and/or the speaker 85 may output an audio signal to notify the user that the target speed has been changed.

The notification device 8 may not include the display 81. The notification device 8 may include both the lamp 84 and the speaker 85, or one of the lamp 84 and the speaker 85. Even in the case where the notification device 8 includes the lamp 84 and does not include the speaker 85, the color of the lamp 84 may be varied or the method of light emission may be varied (e.g., the lamp 84 is turned on, blinked, or turned off) to present the user with various information.

Illustrative preferred embodiments of the present invention have been described.

The drive unit 10 according to a preferred embodiment of the present invention is usable in the electrically assisted wheelchair 1. The drive unit 10 includes the electric motors 25L and 25R that generate driving power to run the electrically assisted wheelchair 1; the torque sensors 50L and 50R that output signals in accordance with torques transmitted from the hand rims 3L and 3R to the wheels 2L and 2R; the speed sensors 26L and 26R that output signals on the running speed of the electrically assisted wheelchair 1; and the controller 100 configured or programmed to control motions of the electric motors 25L and 25R. The controller 100 acquires the output signals from the torque sensors 50L and 50R and the output signals from the speed sensors 26L and 26R. The controller 100 measures a time period in which the first state, where the output signals from the torque sensors 50L and 50R indicate that forward-direction torques applied to the hand rims 3L and 3R each have a value no smaller than the first predetermined value, continues. In the case where the measured time period is the first time period t1 or longer, the controller 100 starts the control of the electric motors 25L and 25R in the cruise control mode by which the electrically assisted wheelchair 1 runs while keeping the running speed at the target speed.

The electrically assisted wheelchair 1 may start running in the cruise control mode by a simple operation, made by the user, of applying power to the hand rims 3L and 3R for a certain time period. The user does not need to make any special operation to start running the electrically assisted wheelchair 1 in the cruise control mode. Therefore, the convenience for the user may be improved.

In a preferred embodiment of the present invention, in the case where the running speed of the electrically assisted wheelchair 1 is lower than the first speed, the controller 100 does not need to start the control of the electric motors 25L and 25R in the cruise control mode. In the case where the running speed is the first speed or higher and the measured time period is the first time period t1 or longer, the controller 100 may start the control of the electric motors 25L and 25R in the cruise control mode.

If the cruise control mode is turned on while the electrically assisted wheelchair 1 runs at a low speed in a small area, for example, indoors, the user may possibly feel uneasy. In the preferred embodiment in which the cruise control mode is set not to be turned on while the running speed is lower than the first speed, the convenience for the user may be improved.

In a preferred embodiment of the present invention, the controller 100 may set, as the target speed, the running speed of the electrically assisted wheelchair 1 at the time when the second time period t2 elapses after the measured time period reaches the first time period t1.

In the preferred embodiment in which the running speed at the time when the second time period t2 elapses is set as the target speed, the running speed obtained as a result of acceleration performed during the second time period t2 may be set as the target speed. Therefore, the target speed may reflect the user's intention to increase the running speed by pushing the hand rims 3L and 3R.

In a preferred embodiment of the present invention, in the case where the running speed keeps increasing after the second time period t2 elapses, the controller 100 may start the control of keeping the running speed at the target speed at the time when the running speed is decreased to the target speed.

In this preferred embodiment, after the second time period t2 elapses, the electrically assisted wheelchair 1 is further accelerated. Then, the electrically assisted wheelchair 1 is mildly decelerated. During the mild deceleration, the control of keeping the running speed at the target speed is started. In this manner, the deviation of the actual change in speed from the change in speed imagined by the user operating the electrically assisted wheelchair 1 may be reduced.

In a preferred embodiment of the present invention, the target speed may be preset.

In the preferred embodiment in which the target speed is preset, the electrically assisted wheelchair 1 may run at the same speed each time. Even in the case where it is difficult to increase the running speed in accordance with the motion of the user pushing the hand rims 3L and 3R, for example, even in the case where the electrically assisted wheelchair 1 is on an upslope, the running speed is increased to the preset target speed by the cruise control. Therefore, the electrically assisted wheelchair 1 may run at the speed intended by the user.

In a preferred embodiment of the present invention, in the case where the running speed keeps increasing after the first time period t1 elapses and becomes higher than the target speed, the controller 100 may start the control of keeping the running speed at the target speed at the time when the running speed is decreased to the target speed.

In this preferred embodiment, after the first time period t1 elapses, the electrically assisted wheelchair 1 is further accelerated. Then, the electrically assisted wheelchair 1 is mildly decelerated. During the mild deceleration, the control of keeping the running speed at the target speed is started. In this manner, the deviation of the actual change in speed from the change in speed imagined by the user operating the electrically assisted wheelchair 1 may be reduced.

In a preferred embodiment of the present invention, in the case where the running speed at the time when the first time period t1 elapses is lower than the target speed, the controller 100 may control the electric motors 25L and 25R such that the running speed becomes the target speed, and then execute the control of keeping the running speed at the target speed.

This makes it unnecessary for the user to make an additional motion of increasing the running speed to the target speed, and thus may improve the convenience for the user.

In a preferred embodiment of the present invention, in the case where the output signals from the torque sensors 50L and 50R indicate that the forward-direction torques applied to the hand rims 3L and 3R each have a value no smaller than the first predetermined value during the control of keeping the running speed at the target speed, the controller 100 may control the electric motors 25L and 25R such that torques, each having a value that is a sum of a torque to keep the running speed at the target speed and a torque in accordance with the level of the output signal, are generated.

Even during the execution of the cruise control, the running speed may be changed in accordance with the push operation made by the user to the hand rims 3L and 3R. Therefore, the electrically assisted wheelchair 1 may run as intended by the user.

The rotation rate of one of the wheels 2L and 2R may be changed in accordance with the push operation made by the user to the corresponding hand rim among the pair of hand rims 3L and 3R. Therefore, the advancing direction of the electrically assisted wheelchair 1 may be changed during the execution of the cruise control.

In a preferred embodiment of the present invention, in the case where the first state, where the output signals from the torque sensors 50L and 50R indicate that the forward-direction torques applied to the hand rims 3L and 3R each have a value no smaller than the first predetermined value, continues for the third time period t3 or longer during the control of keeping the running speed at the target speed, the controller 100 may change the target speed to the running speed at the time when the fourth time period t4 elapses after the first state continues for the third time period t3.

The electrically assisted wheelchair 1 may run in a manner reflecting the user's intention to increase the running speed to be kept in the cruise control mode.

In a preferred embodiment of the present invention, in the case where the second state, where the output signals from the torque sensors 50L and 50R indicate that rearward-direction torques applied to the hand rims 3L and 3R each have a value no smaller than the second predetermined value, continues for the fifth time period t5, the controller 100 may finish the control in the cruise control mode.

The user may finish the cruise control mode by a simple operation of applying power to the hand rims 3L and 3R in the rearward direction for a certain time period. This may improve the convenience for the user.

In general, for significantly changing the advancing direction of, or stopping, the electrically assisted wheelchair 1, the user may make an operation of applying power to the hand rims 3L and 3R in the rearward direction. In the same manner of operation as this, the user may finish the cruise control mode. Therefore, the user may operate the electrically assisted wheelchair 1 by substantially the same sense as for a conventional wheelchair.

In accordance with an operation made by the user to one of the pair of hand rims 3L and 3R in the rearward direction, the cruise control mode may be finished on the corresponding side. In this manner, the advancing direction of the electrically assisted wheelchair 1 may be changed easily.

In a preferred embodiment of the present invention, in the case where the running speed of the electrically assisted wheelchair 1 is decreased to a speed no higher than the second speed, which is lower than the target speed, during the control of keeping the running speed at the target speed, the controller 100 may finish the control in the cruise control mode.

In the case where it becomes difficult to keep the target speed merely by the driving power generated by the electric motors 25L and 25R, for example, in the case where the electrically assisted wheelchair 1 is on an upslope having a large inclining angle, the cruise control mode may be finished and the electrically assisted wheelchair 1 may be run by power that is a sum of the human power and the driving power provided by the electric motors 25L and 25R. In this manner, the electrically assisted wheelchair 1 may keep running.

In a preferred embodiment of the present invention, in the case where a state where a command value to drive the electric motors 25L and 25R is a threshold value or larger continues for the sixth time period t6, the controller 100 may finish the control in the cruise control mode.

In the case where a state where the electric motors 25L and 25R are caused to generate large driving power continues for a certain time period, the cruise control mode may be finished and the electrically assisted wheelchair 1 may be run by power that is a sum of the human power and the driving power provided by the electric motors 25L and 25R. This allows the electrically assisted wheelchair 1 to keep running while the running speed is suppressed from being decreased.

In a preferred embodiment of the present invention, in the case where the battery 7, which supplies electric power to drive the electric motors 25L and 25R, has a remaining capacity smaller than a threshold value, the controller 100 may finish the control in the cruise control mode.

In the case where the remaining capacity of the battery 7 is small, the control in the cruise control mode does not need to be executed. This may suppress the power consumption.

In a preferred embodiment of the present invention, the controller 100 may acquire, from an external device, setting information on whether or not the execution of the control in the cruise control mode is permissible. In the case where the setting information indicates that the execution of the control in the cruise control mode is permissible and the time period in which the first state continues is the first time period t1 or longer, the controller 100 may start the control in the cruise control mode. In the case where the setting information prohibits the execution of the control in the cruise control mode, the controller 100 does not need to execute the control in the cruise control mode.

The external device 200 may set whether or not the execution of the control in the cruise control mode is permissible. For example, while the electrically assisted wheelchair 1 is in an area that is not suitable to running in the cruise control mode, the external device 200 transmits, to the drive unit 10, setting information that prohibits the execution of the control in the cruise control mode. In this manner, the electrically assisted wheelchair 1 may run appropriately in the area.

In a preferred embodiment of the present invention, the controller 100 may acquire, from an external device, target speed information indicating the target speed, and may set a value indicated by the target speed information as the target speed.

In the preferred embodiment in which the external device 200 sets the target speed, the user sitting on the electrically assisted wheelchair 1 does not need to set the target speed. This may improve the convenience for the user.

The external device 200 may transmit, to the drive unit 10, target speed information indicating a target speed varying in accordance with the area in which the electrically assisted wheelchair 1 runs. In this case, the electrically assisted wheelchair 1 may run at the running speed suitable to the area where the electrically assisted wheelchair 1 is running.

In a preferred embodiment of the present invention, the drive unit 10 may further include the notification device 8 to notify the user of the start and the finish of the control in the cruise control mode.

This allows the user to recognize the start and the finish of the control in the cruise control mode.

In a preferred embodiment of the present invention, the target speed may be changeable; and the drive unit 10 may further include the notification device 8 that, in the case where the target speed has been changed, notifies the user of information indicating that the target speed has been changed.

This allows the user to recognize that the target speed has been changed.

The electrically assisted wheelchair 1 according to a preferred embodiment of the present invention includes the drive unit 10; the wheels 2L and 2R to which the driving power generated by the electric motors 25L and 25R is transmitted; and the hand rims 3L and 3R provided on the wheels 2L and 2R.

The electrically assisted wheelchair 1 may start running in the cruise control mode by a simple operation, made by the user, of applying power to the hand rims 3L and 3R for a certain time period. The user does not need to make any special operation to start running the electrically assisted wheelchair 1 in the cruise control mode. Therefore, the convenience for the user may be improved.

A method according to a preferred embodiment of the present invention includes controlling the electrically assisted wheelchair 1. The electrically assisted wheelchair 1 includes the electric motors 25L and 25R to generate driving power to run the electrically assisted wheelchair 1; the wheels 2L and 2R to which the driving power generated by the electric motors 25L and 25R is transmitted; the hand rims 3L and 3R provided on the wheels 2L and 2R; the torque sensors 50L and 50R to output signals in accordance with torques transmitted from the hand rims 3L and 3R to the wheels 2L and 2R; and the speed sensors 26L and 26R to output signals on the running speed of the electrically assisted wheelchair 1. The method includes acquiring the output signals from the torque sensors 50L and 50R and the output signals from the speed sensors 26L and 26R; measuring a time period in which the first state, where the output signals from the torque sensors 50L and 50R indicate that forward-direction torques applied to the hand rims 3L and 3R each have a value no smaller than the first predetermined value, continues; and in the case where the measured time period is the first time period t1 or longer, starting the control of the electric motors 25L and 25R in the cruise control mode by which the electrically assisted wheelchair 1 runs while keeping the running speed at the target speed.

The electrically assisted wheelchair 1 may start running in the cruise control mode by a simple operation, made by the user, of applying power to the hand rims 3L and 3R for a certain time period. The user does not need to make any special operation to start running the electrically assisted wheelchair 1 in the cruise control mode. Therefore, the convenience for the user may be improved.

A computer-readable non-transitory storage medium according to a preferred embodiment of the present invention includes a computer program to cause a computer to control the electrically assisted wheelchair 1. The electrically assisted wheelchair 1 includes the electric motors 25L and 25R to generate driving power to run the electrically assisted wheelchair 1; the wheels 2L and 2R to which the driving power generated by the electric motors 25L and 25R is transmitted; the hand rims 3L and 3R provided on the wheels 2L and 2R; the torque sensors 50L and 50R to output signals in accordance with torques transmitted from the hand rims 3L and 3R to the wheels 2L and 2R; and the speed sensors 26L and 26R to output signals on the running speed of the electrically assisted wheelchair 1. The computer program causes the computer to execute acquiring the output signals from the torque sensors 50L and 50R and the output signals from the speed sensors 26L and 26R; measuring a time period in which the first state, where the output signals from the torque sensors 50L and 50R indicate that forward-direction torques applied to the hand rims 3L and 3R each have a value no smaller than the first predetermined value, continues; and in the case where the measured time period is the first time period t1 or longer, starting the control of the electric motors 25L and 25R in the cruise control mode by which the electrically assisted wheelchair 1 runs while keeping the running speed at the target speed.

The electrically assisted wheelchair 1 may start running in the cruise control mode by a simple operation, made by the user, of applying power to the hand rims 3L and 3R for a certain time period. The user does not need to make any special operation to start running the electrically assisted wheelchair 1 in the cruise control mode. Therefore, the convenience for the user may be improved.

The preferred embodiments of the present invention are especially useful in the field of wheelchairs.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A drive unit usable in an electrically assisted wheelchair, the drive unit comprising:
   an electric motor to generate driving power to run the electrically assisted wheelchair;
   a torque sensor to output a signal in accordance with a torque transmitted from a hand rim to a wheel;
   a speed sensor to output a signal on a running speed of the electrically assisted wheelchair; and
   a controller configured or programmed to control a motion of the electric motor and to:
   acquire the output signal from the torque sensor and the output signal from the speed sensor;
   measure a time period in which a first state, where the output signal from the torque sensor indicates that a forward-direction torque applied to the hand rim has a value no smaller than a first predetermined value, continues; and
   in a case where the measured time period is a first time period or longer, start control of the electric motor in a cruise control mode by which the electrically assisted wheelchair runs while keeping the running speed at a target speed.

2. The drive unit of claim 1, wherein the controller is configured or programmed to:
   in a case where the running speed of the electrically assisted wheelchair is lower than a first speed, not start the control of the electric motor in the cruise control mode; and in a case where the running speed of the electrically assisted wheelchair is the first speed or higher and the measured time period is the first time period or longer, start the control of the electric motor in the cruise control mode.

3. The drive unit of claim 1, wherein the controller is configured or programmed to set, as the target speed, the running speed of the electrically assisted wheelchair at a time when a second time period elapses after the measured time period reaches the first time period.

4. The drive unit of claim 3, wherein in a case where the running speed keeps increasing after the second time period elapses, the controller is configured or programmed to start the control of keeping the running speed at the target speed at a time when the running speed is decreased to the target speed.

5. The drive unit of claim 1, wherein the target speed is preset.

6. The drive unit of claim 5, wherein in a case where the running speed keeps increasing after the first time period elapses and becomes higher than the target speed, the controller is configured or programmed to start the control of keeping the running speed at the target speed at a time when the running speed is decreased to the target speed.

7. The drive unit of claim 5, wherein in a case where the running speed at a time when the first time period elapses is lower than the target speed, the controller is configured or programmed to control the electric motor such that the running speed becomes the target speed, and then execute the control of keeping the running speed at the target speed.

8. The drive unit of claim 1, wherein in a case where the output signal from the torque sensor indicates that the forward-direction torque applied to the hand rim has a value no smaller than the first predetermined value during the control of keeping the running speed at the target speed, the controller is configured or programmed to control the electric motor such that a torque is generated having a value that is a sum of a torque to keep the running speed at the target speed and a torque in accordance with a level of the output signal from the torque sensor.

9. The drive unit of claim 1, wherein in a case where the first state, where the output signal from the torque sensor indicates that the forward-direction torque applied to the hand rim has a value no smaller than the first predetermined value, continues for a third time period or longer during the control of keeping the running speed at the target speed, the controller is configured or programmed to change the target speed to the running speed at a time when a fourth time period elapses after the first state continues for the third time period.

10. The drive unit of claim 1, wherein in a case where a second state, where the output signal from the torque sensor indicates that a rearward-direction torque applied to the hand rim has a value no smaller than a second predetermined value, continues for a fifth time period, the controller is configured or programmed to finish the control in the cruise control mode.

11. The drive unit of claim 1, wherein in a case where the running speed of the electrically assisted wheelchair is decreased to a speed no higher than a second speed, which is lower than the target speed, during the control of keeping the running speed at the target speed, the controller is configured or programmed to finish the control in the cruise control mode.

12. The drive unit of claim 1, wherein in a case where a state where a command value to drive the electric motor is a threshold value or larger continues for a sixth time period, the controller is configured or programmed to finish the control in the cruise control mode.

13. The drive unit of claim 1, wherein in a case where a battery that supplies electric power to drive the electric motor has a remaining capacity smaller than a threshold value, the controller is configured or programmed to finish the control in the cruise control mode.

14. The drive unit of claim 1, wherein the controller is configured or programmed to:
   acquire, from an external device, setting information on whether or not execution of the control in the cruise control mode is permissible;
   in a case where the setting information indicates that the execution of the control in the cruise control mode is permissible and a time period in which the first state continues is the first time period or longer, start the control in the cruise control mode; and
   in a case where the setting information prohibits the execution of the control in the cruise control mode, not execute the control in the cruise control mode.

15. The drive unit of claim 1, wherein the controller is configured or programmed to:
   acquire from an external device target speed information indicating the target speed; and
   set a value indicated by the target speed information as the target speed.

16. The drive unit of claim 1, further comprising:
   a notifier to notify a user of the start and the finish of the control in the cruise control mode.

17. The drive unit of claim 1, wherein
   the target speed is changeable; and
   the drive unit further includes a notifier to, in a case where the target speed has been changed, notify a user of information indicating that the target speed has been changed.

18. The drive unit of claim 1, wherein the torque sensor is located in the wheel.

19. The drive unit of claim 1, wherein the torque transmitted from the hand rim to the wheel is directly detected by the torque sensor.

20. An electrically assisted wheelchair comprising:
   the drive unit of claim 1;
   the wheel to which the driving power generated by the electric motor is transmitted; and
   the hand rim provided on the wheel.

21. A method for controlling an electrically assisted wheelchair including an electric motor to generate driving power to run the electrically assisted wheelchair, a wheel to which the driving power generated by the electric motor is transmitted, a hand rim provided on the wheel, a torque sensor to output a signal in accordance with a torque transmitted from the hand rim to the wheel, and a speed sensor to output a signal on a running speed of the electrically assisted wheelchair, the method comprising:
   acquiring the output signal from the torque sensor and the output signal from the speed sensor;
   measuring a time period in which a first state, where the output signal from the torque sensor indicates that a forward-direction torque applied to the hand rim has a value no smaller than a first predetermined value, continues; and
   in response to the measured time period being a first time period or longer, starting control of the electric motor in a cruise control mode by which the electrically assisted wheelchair runs while keeping the running speed at a target speed.

22. A computer-readable non-transitory storage medium including a computer program to cause a computer to control an electrically assisted wheelchair including an electric motor to generate driving power to run the electrically assisted wheelchair, a wheel to which the driving power generated by the electric motor is transmitted, a hand rim provided on the wheel, a torque sensor to output a signal in accordance with a torque transmitted from the hand rim to the wheel, and a speed sensor to output a signal on a running speed of the electrically assisted wheelchair, the computer program causing the computer to execute:

acquiring the output signal from the torque sensor and the output signal from the speed sensor;

measuring a time period in which a first state, where the output signal from the torque sensor indicates that a forward-direction torque applied to the hand rim has a value no smaller than a first predetermined value, continues; and in a case where the measured time period is a first time period or longer, starting control of the electric motor in a cruise control mode by which the electrically assisted wheelchair runs while keeping the running speed at a target speed.

* * * * *